US007754756B2

(12) United States Patent
Walter et al.

(10) Patent No.: US 7,754,756 B2
(45) Date of Patent: Jul. 13, 2010

(54) INDOL-CONTAINING BETA-AGONISTS, METHODS FOR THE PREPARATION THEREOF AND THEIR USE AS PHARMACEUTICAL COMPOSITIONS

(75) Inventors: Rainer Walter, Biberach (DE); Bradford S. Hamilton, Biberach (DE); Thomas Trieselmann, Warthausen (DE); Matthew R. Netherton, Danbury, CT (US); Marco Santagostino, Mittelbiberach (DE); Ingo Konetzki, Warthausen (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 634 days.

(21) Appl. No.: 11/550,830

(22) Filed: Oct. 19, 2006

(65) Prior Publication Data

US 2007/0105906 A1 May 10, 2007

(30) Foreign Application Priority Data

Oct. 28, 2005 (DE) ........................ 10 2005 052 127

(51) Int. Cl.
*A61K 31/4045* (2006.01)
*A61K 31/404* (2006.01)
*C07D 209/24* (2006.01)
*C07D 209/18* (2006.01)
*C07D 413/02* (2006.01)

(52) U.S. Cl. .................... 514/415; 514/414; 514/235.2; 548/509; 548/469; 548/483; 544/143

(58) Field of Classification Search ................ 514/414, 514/415, 235.2; 548/509, 469, 483; 544/143
See application file for complete search history.

(56) References Cited

U.S. PATENT DOCUMENTS

| 2,943,090 | A | 6/1960 | Semb et al. |
| 3,092,636 | A | 6/1963 | Heinzelman et al. |
| 4,215,119 | A | 7/1980 | Mentrup et al. |
| 4,647,563 | A | 3/1987 | Schromm et al. |
| 6,667,342 | B1 | 12/2003 | Clarke et al. |
| 7,214,698 | B2 | 5/2007 | Trieselmann et al. |
| 2005/0020602 | A1 | 1/2005 | Miyoshi et al. |
| 2005/0245526 | A1 | 11/2005 | Trieselmann et al. |
| 2007/0112033 | A1 | 5/2007 | Trieselmann et al. |
| 2008/0103138 | A1 | 5/2008 | Trieselmann et al. |
| 2008/0234278 | A1 | 9/2008 | Trieselmann et al. |
| 2008/0269281 | A1 | 10/2008 | Trieselmann et al. |
| 2008/0300290 | A1 | 12/2008 | Walter et al. |

FOREIGN PATENT DOCUMENTS

| CA | 2504213 A1 | 5/2004 |
| CA | 2564980 A1 | 11/2005 |
| DE | 2115926 | 10/1972 |
| EP | 0008653 | 3/1980 |
| EP | 0177245 A2 | 4/1986 |
| EP | 0659737 | 4/1986 |
| EP | 1447400 A1 | 8/2004 |
| EP | 1277736 | 2/2009 |
| GB | 1200886 | 8/1970 |
| GB | 2356197 | 5/2001 |
| WO | 9529159 A1 | 11/1995 |
| WO | 9721665 A1 | 6/1997 |
| WO | 0162705 | 8/2001 |
| WO | 0183452 | 11/2001 |
| WO | 2004039784 A1 | 5/2004 |
| WO | 2005108373 A1 | 11/2005 |

OTHER PUBLICATIONS

Clifton et al.; Arylethanolamines derived from salicylamide with .alpha.- and .beta.-adrenoceptor blocking activities. Preparation of labetalol, its enantiomers and related salicylamides; Journal of Medicinal Chemistry; 1982; vol. 25; No. 6; pp. 670-679.
Kawashima Kazu; Publication No. 08165276; Publication Date Jun. 25, 1996; 2-akylannino-l-phenylethanol derivative; Patent Abstracts of Japan; vol. 1996; No. 10.
Arch; B3-Andrenoceptor agonists: potential, pitfalls and progress; European Journal of Pharmacology; 2002; vol. 440; pp. 99-107.
Moffett; New compounds with possible pharmacological activity; Journal of Chemical and Engineering Data; 1980; vol. 25; No. 2; pp. 176-183.
Thompson et al.; Protein Conformational Misfolding and Amyloid Formation: Characteristics of a New Class of Disorders that Include Alzheimer's and Prion Diseases; Current Medicinal Chemistry; 2002; vol. 9; pp. 1751-1762.
International Search Report, Form PCT/ISA/210, for corresponding PCT/EP2006/067874; mailed on Jan. 5, 2007.
International Search Report, Form PCT/ISA/210, for corresponding PCT/EP2006/067875; mailed on Mar. 30, 2007.

(Continued)

Primary Examiner—Rebecca L Anderson
Assistant Examiner—Jason M Nolan
(74) Attorney, Agent, or Firm—Michael P. Morris; Mary-Ellen M. Devlin; Alan R. Stempel

(57) ABSTRACT

The present invention relates to new beta-agonists of general formula (I)

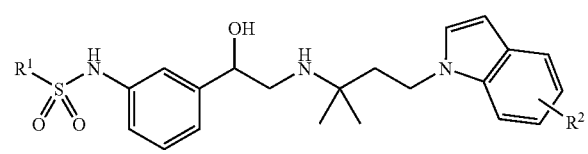

wherein the groups $R^1$ and $R^2$ have the meanings given in the claims and specification, the tautomers, racemates, enantiomers, diastereomers, solvates, hydrates, mixtures thereof, the prodrugs thereof and the salts thereof, particularly the physiologically acceptable salts thereof with inorganic or organic acids or bases, methods of preparing these compounds and their use as pharmaceutical compositions.

16 Claims, No Drawings

OTHER PUBLICATIONS

International Search Report, Form PCT/ISA/210, for corresponding PCT/EP2006/067868; mailed on Jan. 9, 2007.
Harada, et al; Discovery of a Novel and Potent Human and Rat B3-Adrenergic Receptor Agonist, [3-[(2R)-[[(2R)-(3-Chlorophenyl)-2-hydroxyethyl]amino]propyl]-1H-indol-7-yloxy]acetic Acid; Chemical & Pharmaceutical Bulletin; Feb. 2005; vol. 53; No. 2, pp. 184-198.

Weyer, C., et al. "Increase in Insulin Action and Fat Oxidation After Treatment With CL 316,243, a Highly Selective $\beta_3$-Adrenoceptor Agonist in Humans" Diabetes 47:1555-1561 (Oct. 1988).
Hicks, A., et al. "GW427353 (Solabegron), a Novel, Selective $\beta_3$-Adrenergic Receptor Agonist, Evokes Bladder Relation and Increases Micturition Reflex Threshold in the Dog" The Journal of Pharmacology and Experimental Therapeutics, 323(1):202-209 (2007).

INDOL-CONTAINING BETA-AGONISTS, METHODS FOR THE PREPARATION THEREOF AND THEIR USE AS PHARMACEUTICAL COMPOSITIONS

The present invention relates to new beta-agonists of general formula (I)

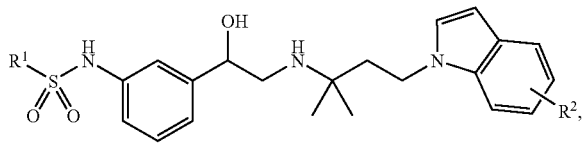

wherein the groups $R^1$ and $R^2$ are as defined below, the tautomers, racemates, enantiomers, diastereomers, solvates, hydrates, mixtures thereof, the prodrugs thereof and the salts thereof, particularly the physiologically acceptable salts thereof with inorganic or organic acids or bases, methods for preparing these compounds and their use as pharmaceutical compositions.

BACKGROUND TO THE INVENTION

The treatment of type II diabetes and obesity is based primarily on reducing calorie intake and increasing physical activity. These methods are rarely successful in the longer term.

It is known that beta-3 receptor agonists have a significant effect on lipolysis, thermogenesis and the serum glucose level in animal models of type II diabetes (Arch J R. beta(3)-Adrenoceptor agonists: potential, pitfalls and progress, Eur J Pharmacol. 2002 Apr. 12; 440(2-3):99-107).

Compounds which are structurally similar to the compounds according to the invention and their broncholytic, spasmolytic and antiallergic activities were disclosed in DE 2833140, for example.

The aim of the present invention is to provide selective beta-3 agonists which can be used to prepare pharmaceutical compositions for the treatment of obesity and type II diabetes.

DETAILED DESCRIPTION OF THE INVENTION

Surprisingly it has been found that compounds of general formula (I) wherein the groups $R^1$ and $R^2$ are defined as hereinafter are effective as selective beta-3 agonists. Thus, the compounds according to the invention may be used to treat diseases connected with the stimulation of beta-3-receptors.

The present invention therefore relates to compounds of general formula (I)

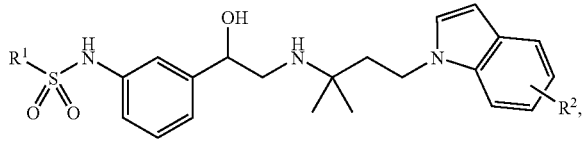

wherein $R^1$ denotes a phenyl group, which may be mono- or disubstituted by fluorine, chlorine or bromine atoms or methyl, methoxy, trifluoromethoxy or difluoromethoxy groups, wherein the substituents may be identical or different, or a heteroaryl group selected from among pyridinyl and thienyl, and $R^2$ denotes a hydrogen, fluorine, chlorine, bromine or iodine atom, a nitro, cyano, trifluoromethoxy, difluoromethoxy, carboxy, 2,2,2-trifluoro-acetyl group, $C_{1-3}$-alkylsulphanyl, $C_{1-3}$-alkylsulphinyl, $C_{1-3}$-alkylsulphonyl, tetrazolyl, 5-oxo-4,5-dihydro-[1,3,4]oxadiazol-2-yl, or 5-oxo-2,5-dihydro-[1,2,4]oxadiazol-3-yl group, an amino group, which may be substituted by a carboxycarbonyl, aminocarbonyl, $C_{1-6}$-alkyl-aminocarbonyl, phenylaminocarbonyl, $C_{1-6}$-alkyl-carbonyl, benzyloxy-$C_{1-3}$-alkyl-carbonyl, cyano-$C_{1-3}$-alkyl-carbonyl, $C_{3-7}$-cycloalkyl-carbonyl or $C_{1-3}$-alkylsulphonyl group, wherein the above-mentioned $C_{1-6}$-alkyl-carbonyl group may be straight-chain or branched and may be substituted by an amino group in the alkyl moiety, a $C_{1-3}$-alkyl group, which may be substituted independently of one another by one or two trifluoromethyl, hydroxy, carboxy or $C_{1-6}$-alkyloxy-carbonyl groups, a $C_{2-3}$-alkenyl group, which may be substituted by a carboxy group, a $C_{1-3}$-alkyloxy group, which may be substituted by a carboxy or $C_{1-3}$-alkyloxy-carbonyl group, a $C_{1-3}$-alkyl-carbonyl group, which is substituted by a $C_{1-3}$-alkylsulphonyl group, $C_{1-6}$-alkyloxy-carbonyl group, which may be substituted in the alkyl moiety by a di-($C_{1-3}$-alkyl)-amino-carbonyl, $C_{1-6}$-alkyl-carbonyloxy, $C_{1-6}$-alkyloxy-carbonyloxy or pyridinyl group or by a 2-oxo-[1,3]dioxolyl group optionally substituted by a $C_{1-3}$-alkyl group, $C_{2-6}$-alkyloxy-carbonyl group, which is substituted in the alkyl moiety from position 2 by a di-($C_{1-4}$-alkyl)-amino, N—($C_{1-3}$-alkyl)-N-benzyl-amino or $C_{1-3}$-alkyloxy-$C_{1-3}$-alkyloxy group or by a 3- to 7-membered cycloalkyleneimino group, wherein in the above-mentioned 5- to 7-membered cycloalkyleneimino group one or two methylene groups independently of one another may be replaced by an oxygen or sulphur atom and/or a carbonyl, sulphonyl or an —N($C_{1-3}$-alkyl)-group, an aminocarbonyl group, which may be substituted at the nitrogen atom independently of one another by one or two groups selected from among cyano, hydroxy, $C_{1-6}$-alkyl, $C_{3-7}$-cycloalkyl, $C_{1-3}$-alkoxy, amino, di-($C_{1-3}$-alkyl)-amino, (4-methyl-phenyl)-sulphonyl, wherein the above-mentioned alkyl group may be straight-chain or branched and may be substituted by one to three fluorine atoms or by a carboxy, $C_{1-3}$-alkoxy-carbonyl, $C_{3-7}$-cycloalkyl or $C_{1-3}$-alkylsulphonyl group, a carbonyl group, which is substituted by a 3- to 7-membered cycloalkyleneimino group, wherein in the above-mentioned 5- to 7-membered cycloalkyleneimino group a methylene group may be replaced by an oxygen or sulphur atom or a carbonyl or sulphonyl group, or a group of formula

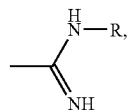

wherein R denotes a hydrogen atom or a hydroxy group, wherein the alkyl groups contained in the above-mentioned groups may each be straight-chain or branched, as well as the prodrugs thereof, tautomers, racemates, enantiomers, diastereomers, solvates, hydrates, mixtures thereof and the salts thereof.

Preferred compounds of general formula (I) are those wherein $R^2$ is as hereinbefore defined and $R^1$ denotes a phenyl group, which may be substituted by a fluorine, chlorine or bromine atom or a methyl, methoxy, trifluoromethoxy or difluoromethoxy groups, the tautomers, enantiomers, diastereomers, mixtures thereof and the salts thereof.

Particularly preferred are those compounds of general formula (I), wherein $R^2$ is as hereinbefore defined and $R^1$ denotes a phenyl group, the tautomers, enantiomers, diastereomers, mixtures thereof and the salts thereof.

Most particularly preferred are those compounds of general formula (I), wherein $R^2$ denotes a hydrogen atom or a cyano, carboxy, $C_{1-4}$-alkyloxy-carbonyl, tetrazolyl, 5-oxo-2,5-dihydro-[1,2,4]oxadiazol-3-yl or 5-oxo-4,5-dihydro-[1,3,4]oxadiazol-2-yl group, wherein the above mentioned $C_{2-4}$-alkyloxy-carbonyl groups in the alkyl moiety may be substituted from position 2 by a di-($C_{1-4}$-alkyl)-amino group and an amino group, which may be substituted by a carboxycarbonyl, aminocarbonyl, $C_{1-3}$-alkylcarbonyl or cyanoacetyl group, an aminocarbonyl group, which may independently of one another be substituted at the nitrogen atom by one or two groups selected from among hydroxy, methyl, amino, and cyclopropylmethyl, or a carbonyl group, which is substituted by a morpholin-4-yl, pyrrolidin-1-yl or 1,1-dioxo-1-thiomorpholin-4-yl, wherein the alkyl group contained in the above mentioned groups may in each case be straight-chain or branched, the tautomers, enantiomers, diastereomers, mixtures thereof and the salts thereof.

Mention should be made of those compounds of general formula (I), wherein $R^1$ denotes a phenyl group, which may be mono- or disubstituted by fluorine, chlorine or bromine atoms or methyl, methoxy, trifluoromethoxy or difluoromethoxy groups, wherein the substituents may be identical or different or a heteroaryl group selected from among pyridinyl and thienyl, and $R^2$ denotes a hydrogen, fluorine, chlorine, bromine or iodine atom or an amino, cyano, methoxy, trilfluormethoxy, difluoromethoxy, carboxy, $C_{1-6}$-alkyloxy-carbonyl, aminocarbonyl, $C_{1-3}$-alkylsulphinyl, $C_{1-3}$-alkylsulphonyl, tetrazolyl or 1,2,4-oxadiazol-5-on-3-yl group, wherein the above mentioned $C_{2-6}$-alkyloxy-carbonyl groups in the alkyl moiety may be substituted from position 2 by a di-($C_{1-3}$-alkyl)-amino, di-($C_{1-3}$-alkyl)-aminocarbonyl or 4-methyl-1,3-dioxol-2-on-3-yl group and the aminocarbonyl group at the nitrogen atom may be substituted independently of one another by one or two groups selected from among $C_{1-3}$-alkyl, $C_{1-3}$-alkoxy, hydroxy and cyano, wherein the alkyl groups contained in the above-mentioned groups may each be straight-chain or branched, as well as the prodrugs thereof, tautomers, racemates, enantiomers, diastereomers, solvates, hydrates, mixtures thereof and the salts thereof.

Mention should also be made of those compounds of general formula (I), wherein $R^2$ is as hereinbefore defined and $R^1$ denotes a phenyl group, which may be substituted by a fluorine, chlorine or bromine atom or a methyl, methoxy, trifluoromethoxy or difluoromethoxy groups, the tautomers, enantiomers, diastereomers, mixtures thereof and the salts thereof.

Particular mention should be made of those compounds of general formula (I), wherein $R^2$ is as hereinbefore defined and $R^1$ denotes a phenyl group, the tautomers, enantiomers, diastereomers, mixtures thereof and the salts thereof.

Most particular mention should be made of those compounds of general formula (I), wherein $R^2$ denotes a hydrogen, fluorine, chlorine or bromine atom or an amino, cyano, carboxy, $C_{1-4}$-alkyloxy-carbonyl, aminocarbonyl, $C_{1-3}$-alkylsulphinyl, $C_{1-3}$-alkylsulphonyl, tetrazolyl or 1,2,4-oxadiazol-5-on-3-yl group, wherein the above mentioned $C_{2-4}$-alkyloxy-carbonyl groups in the alkyl moiety may be substituted from position 2 by a di-($C_{1-3}$-alkyl)-amino, di-($C_{1-3}$-alkyl)-aminocarbonyl or 4-methyl-1,3-dioxol-2-on-3-yl-group and the aminocarbonyl group at the nitrogen atom may be substituted independently of one another by one or two groups selected from among $C_{1-3}$-alkyl, $C_{1-3}$-alkoxy, hydroxy and cyano, and wherein the alkyl group contained in the above mentioned groups may each be straight-chain or branched, the tautomers, enantiomers, diastereomers, mixtures thereof and the salts thereof.

A preferred sub-group relates to those compounds of general formula (I), wherein $R^1$ and $R^2$ are as hereinbefore defined and wherein the group $R^2$ is in position 5 or 6, particularly in position 5 of the indole, the tautomers, enantiomers, diastereomers, mixtures thereof and the salts thereof.

A second preferred sub-group relates to the (R)-enantiomer of formula (Ia)

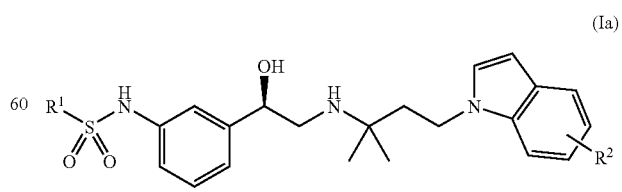

(Ia)

of the compounds according to the invention, wherein $R^1$ and $R^2$ are as hereinbefore defined, and the salts thereof.

A third preferred sub-group relates to the (S)-enantiomer of formula (Ib)

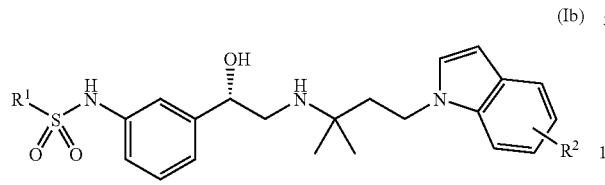

of the compounds according to the invention, wherein R¹ and R² are as hereinbefore defined, and the salts thereof.

Particular mention should be made of the following compounds:

N-(1-{3-[(R)-2-[3-(phenylsulphonylamino)-phenyl]-2-hydroxy-ethylamino]-3-methyl-butyl}-1H-indol-5-yl)-2-cyano-acetamide 1-{3-[(R)-2-[3-(phenylsulphonylamino)-phenyl]-2-hydroxy-ethylamino]-3-methyl-butyl}-1H-indole-5-carboxylic acid-cyclopropyl methyl-amide N-[3-((R)-2-{1,1-dimethyl-3-[5-(morpholin-4-ylcarbonyl)-indol-1-yl]-propylamino}-1-hydroxy-ethyl)-phenyl]-benzenesulphonamide 1-{3-[(R)-2-[3-(phenylsulphonylamino)-phenyl]-2-hydroxy-ethylamino]-3-methyl-butyl}-1H-indole-5-carboxylic acid N-(3-{(R)-2-[1,1-dimethyl-3-(5-ureido-indol-1-yl)-propylamino]-1-hydroxy-ethyl}-phenyl)-benzenesulphonamide)

[2-(morpholin-4-yl)-ethyl]1-{3-[(R)-2-[3-(phenylsulphonylamino)-phenyl]-2-hydroxy-ethylamino]-3-methyl-butyl}-1H-indole-5-carboxylate N-(3-{(R)-2-[3-(5-amino-indol-1-yl)-1,1-dimethyl-propylamino]-1-hydroxy-ethyl}-phenyl)-benzenesulphonamide N-(3-{(R)-2-[3-(5-hydrazinocarbonyl-indol-1-yl)-1,1-dimethyl-propylamino]-1-hydroxy-ethyl}-phenyl)-benzenesulphonamide (2-dimethylamino-ethyl) 1-{3-[(R)-2-[3-(phenylsulphonylamino)-phenyl]-2-hydroxy-ethylamino]-3-methyl-butyl}-1H-indole-5-carboxylate N-(1-{3-[(R)-2-[3-(phenylsulphonylamino)-phenyl]-2-hydroxy-ethylamino]-3-methyl-butyl}-1H-indol-5-yl)-oxalamidic acid and the enantiomers and salts thereof.

In another aspect the invention relates to compounds of general formula (I) for use as pharmaceutical compositions.

In another aspect the invention relates to compounds of general formula (I) for use as pharmaceutical compositions with a selective beta-3-agonistic activity.

The invention also relates to compounds of general formula (I) for preparing a pharmaceutical composition for the treatment and/or prevention of diseases connected with the stimulation of beta-3-receptors.

The invention further relates to a method for the treatment and/or prevention of diseases connected with the stimulation of beta-3-receptors, in which a patient is given an effective amount of a compound of general formula I.

The invention further relates to a pharmaceutical composition containing as active substance one or more compounds of general formula (I), optionally combined with conventional excipients and/or carriers.

The invention further relates to a pharmaceutical composition containing as active substance one or more compounds of general formula (I) or the physiologically acceptable salts thereof and one or more active substances selected from among antidiabetics, inhibitors of protein tyrosinephosphatase 1, substances which influence deregulated glucose production in the liver, lipid lowering agents, cholesterol absorption inhibitors, HDL-raising compounds, active substances for the treatment of obesity and modulators or stimulators of the adrenergic system via alpha 1 and alpha 2 as well as beta 1, beta 2 and beta 3 receptors.

The invention also relates to a process for preparing a compound of general formula (I),

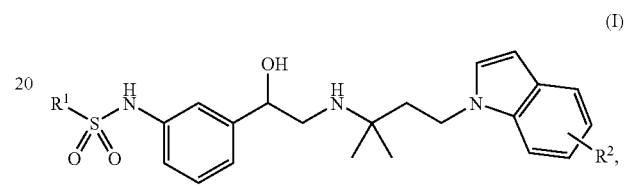

wherein

R¹ and R² may have the meanings given hereinbefore, wherein a compound of formula (II)

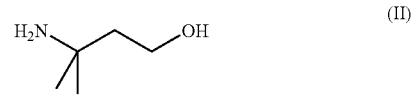

is converted by means of a chlorinating agent into a compound of formula (IIIa)

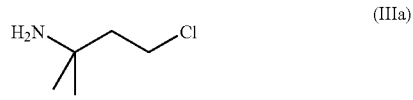

or a compound of the above formula (II) after the introduction of a suitable protective group at the amino function is converted by cyclisation with thionyl chloride and subsequent oxidation into a compound of formula (IIIb)

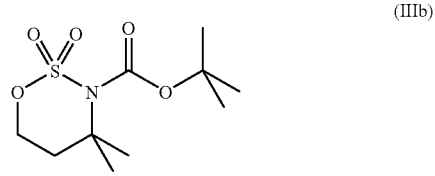

the compound of formula (IIIa) or (IIIb), optionally provided with an amino protecting group, is reacted with an indole (IV),

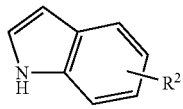

(IV)

wherein R² may have the meanings given hereinbefore, and the product of formula (V)

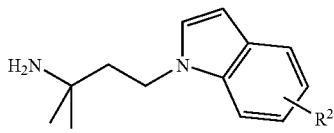

(V)

wherein R² may have the meanings given hereinbefore, is reacted with a compound of formula (VIa) or (VIb)

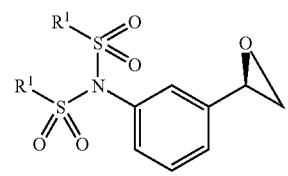

(VIa)

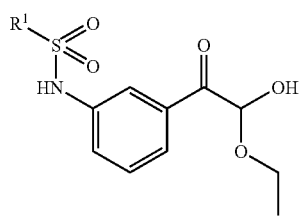

(VIb)

wherein R² has the meaning given hereinbefore, and then optionally a desulphonation or enantiomer separation is carried out.

The reaction with the compound (VIb) leads to the racemate, whereas the synthesis with the compound (VIa) yields the respective (R)-enantiomer. An analogous reaction with the enantiomer to (VIa), leading to the (S)-enantiomer, is, of course, also conceivable.

The preparation of the compound of general formula (IIIb) may for example be carried out according to the method described in this application or as described in International Application WO 03/037327, pages 82-83.

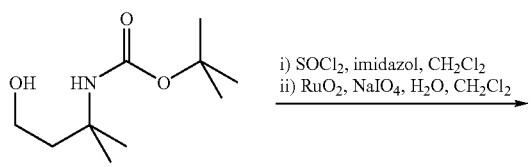

i) SOCl₂, imidazol, CH₂Cl₂
ii) RuO₂, NaIO₄, H₂O, CH₂Cl₂

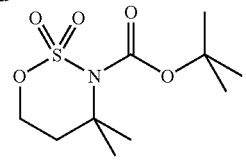

(IIIb)

In another aspect the invention relates to an improved process for preparing the compound (IIIb), which is described by way of example in the experimental section.

The term alkyl groups, including alkyl groups which are a part of other groups, unless otherwise stated, denotes branched and unbranched alkyl groups with 1 to 10 carbon atoms, while groups with 1 to 6 carbon atoms are preferred. Particularly preferred are alkyl groups with 1 to 4 carbon atoms, particularly those with 1 or 2 carbon atoms. Examples include: methyl, ethyl, propyl, butyl, pentyl, hexyl, heptyl, octyl, nonyl and decyl. Unless otherwise stated, the above-mentioned terms propyl, butyl, pentyl, hexyl, heptyl, octyl, nonyl and decyl include all the possible isomeric forms. For example, the term propyl includes the two isomeric groups n-propyl and iso-propyl, the term butyl includes n-butyl, iso-butyl, sec. butyl and tert.-butyl, the term pentyl includes iso-pentyl, neopentyl, etc.

In the above-mentioned alkyl groups one or more hydrogen atoms may optionally be replaced by other groups. For example, these alkyl groups may be substituted by the halogen atoms fluorine, chlorine, bromine or iodine. Preferably the substituents are fluorine or chlorine. The substituent fluorine is most preferred. All the hydrogen atoms of the alkyl group may optionally also be replaced.

Similarly, in the above-mentioned alkyl groups, unless otherwise stated, one or more hydrogen atoms may optionally be replaced, for example, by OH, $NO_2$, CN or an optionally substituted group selected from among —O—$C_1$-$C_5$-alkyl, preferably methoxy or ethoxy, —O—($C_6$-$C_{14}$-aryl), preferably phenyloxy, —O-heteroaryl, preferably —O-thienyl, —O-thiazolyl, —O-imidazolyl, —O-pyridyl, —O-pyrimidyl or —O-pyrazinyl, saturated or unsaturated —O-heterocycloalkyl, preferably —O-pyrazolyl, —O-pyrrolidinyl, —O-piperidinyl, —O-piperazinyl or —O-tetrahydro-oxazinyl, $C_6$-$C_{14}$-aryl, preferably phenyl, heteroaryl, preferably thienyl, thiazolyl, imidazolyl, pyridyl, pyrimidyl or pyrazinyl, saturated or unsaturated heterocycloalkyl, preferably pyrazolyl, pyrrolidinyl, piperidinyl, piperazinyl or tetrahydro-oxazinyl, an amine group, preferably methylamine, benzylamine, phenylamine or heteroarylamine, saturated or unsaturated bicyclic ring systems, preferably benzimidazolyl and $C_3$-$C_8$-cycloalkyl, preferably cyclohexyl or cyclopropyl.

Alkenyl groups as well as alkenyl groups which are a part of other groups denote branched and unbranched alkyl groups with 1 to 10 carbon atoms, preferably 1 to 6, particularly preferably 1 to 4 carbon atoms, which contain at least one carbon-carbon double bond. Examples include: ethenyl, propenyl, methylpropenyl, butenyl, pentenyl, hexenyl, heptenyl, methylheptenyl, octenyl, nonenyl and decenyl. Unless stated otherwise, the terms propenyl, butenyl, pentenyl, hexenyl, heptenyl, octenyl, nonenyl and decenyl used above include all the possible isomeric forms. For example, the term butenyl includes the isomeric groups but-1-enyl, but-2-enyl and but-3-enyl, etc. In the above-mentioned alkenyl groups one or more hydrogen atoms may optionally be replaced by other groups. For example, these alkenyl groups may be substituted by the halogen atoms fluorine, chlorine, bromine or iodine. The substituents fluorine or chlorine are preferred. The substituent fluorine is particularly preferred. It is also possible to replace all the hydrogen atoms of the alkenyl group.

Alkynyl groups as well as alkynyl groups which are a part of other groups denote branched and unbranched alkyl groups with 1 to 10 carbon atoms, preferably 1 to 6, particularly preferably 1 to 4 carbon atoms which contain at least one carbon-carbon triple bond. Examples include: ethynyl, propynyl, butynyl, pentynyl, hexynyl, heptynyl, octynyl, nonynyl and decynyl. Unless otherwise mentioned, the terms propynyl, butynyl, pentynyl, hexynyl, heptynyl, octynyl, nonynyl and decynyl used above include all the possible isomeric forms. For example, the term butynyl includes the isomeric groups but-1-ynyl, but-2-ynyl and but-3-ynyl, etc.

In the above-mentioned alkynyl groups one or more hydrogen atoms may optionally be replaced by other groups. For example, these alkynyl groups may be substituted by the halogen atoms fluorine, chlorine, bromine or iodine. The substituents fluorine or chlorine are preferred. The substituent fluorine is particularly preferred. It is also possible to replace all the hydrogen atoms of the alkynyl group.

The term aryl denotes an aromatic ring system with 6 to 18 carbon atoms, preferably 6 to 14 carbon atoms, preferably 6 or 10 carbon atoms, most preferably phenyl, which may optionally be substituted and may preferably carry one or more of the following substituents: OH, $NO_2$, CN, —$OCHF_2$, —$OCF_3$, —$NH_2$, —NH-alkyl, —N(alkyl)-alkyl, —NH-aryl, —N(alkyl)-aryl, —NHCO-alkyl, —NHCO-aryl, —N(alkyl)-CO-alkyl, —N(alkyl)-CO-aryl, —$NHSO_2$-alkyl, —$NHSO_2$—N(alkyl)$_2$, —$NHSO_2$-aryl, —N(alkyl)-$SO_2$-alkyl, —N(alkyl)-$SO_2$-aryl, —$CO_2$-alkyl, —$SO_2$-alkyl, —$SO_2$-aryl, —CON H(OH), —CONH-alkyl, —CON H-aryl, —CON(alkyl)-alkyl, —CON(alkyl)-aryl, —$SO_2$NH-alkyl, —$SO_2$NH-aryl, —$SO_2$N(alkyl)-alkyl, —$SO_2$N(alkyl)-aryl, —O-alkyl, —O-aryl —S-alkyl, —S-aryl, tetrazolyl, halogen, for example fluorine, chlorine, bromine or iodine, preferably fluorine or chlorine, particularly fluorine, $C_1$-$C_{10}$-alkyl, preferably $C_1$-$C_5$-alkyl, particularly preferably $C_1$-$C_3$-alkyl, most particularly preferably methyl or ethyl, —O—($C_1$-$C_3$-alkyl), preferably methoxy or ethoxy, —COOH or —$CONH_2$.

Examples of heteroaryl groups are 5- to 10-membered mono- or bicyclic heteroaryl rings wherein one to three carbon atoms in each case may be replaced by a heteroatom selected from among oxygen, nitrogen or sulphur. Examples include furan, thiophene, pyrrole, pyrazole, imidazole, triazole, tetrazole, pyridine, pyridazine, pyrimidine, pyrazine, triazine, oxazole, isoxazole, thiazole, thiadiazole, oxadiazole, while each of the above-mentioned heterocycles may optionally also be annellated to a benzene ring, such as benzimidazole, and these heterocycles may optionally be substituted and preferably carry one or more of the following substituents: OH, $NO_2$, CN, —$NH_2$, —NH-alkyl, —N(alkyl)-alkyl, —NH-aryl, —N(alkyl)-aryl, —NHCO-alkyl, —NHCO-aryl, —N(alkyl)-CO-alkyl, —N(alkyl)-CO-aryl, —$NHSO_2$-alkyl, —$NHSO_2$-aryl, —N(alkyl)-$SO_2$-alkyl, —N(alkyl)-$SO_2$-aryl, —$CO_2$-alkyl, —$SO_2$-alkyl, —$SO_2$-aryl, —CONH-alkyl, —CONH-aryl, —CON(alkyl)-alkyl, —CON(alkyl)-aryl, —$SO_2$NH-alkyl, —$SO_2$NH-aryl, —$SO_2$N(alkyl)-alkyl, —$SO_2$N(alkyl)-aryl, —O-alkyl, —O-aryl —S-alkyl, —S-aryl, —$CONH_2$, halogen, preferably fluorine or chlorine, $C_1$-$C_{10}$-alkyl, preferably $C_1$-$C_5$-alkyl, preferably $C_1$-$C_3$-alkyl, particularly preferably methyl or ethyl, —O—($C_1$-$C_3$-alkyl), preferably methoxy or ethoxy, —COOH, —$COOCH_3$, —$CONH_2$, —SO-alkyl, —$SO_2$-alkyl, —$SO_2$H, —$SO_3$-alkyl or optionally substituted phenyl.

Examples of cycloalkyl groups are saturated or unsaturated cycloalkyl groups with 3 to 8 carbon atoms, for example cyclopropyl, cyclobutyl, cyclopentyl, cyclopentenyl, cyclohexyl, cyclohexenyl, cycloheptyl or cyclooctyl, preferably cyclopropyl, cyclopentyl or cyclohexyl, while each of the above-mentioned cycloalkyl groups may optionally also carry one or more substituents or be annellated to a benzene ring.

Unless otherwise stated in the definitions, examples of heterocycloalkyl or heterocyclyl groups include 5-, 6- or 7-membered, saturated or unsaturated heterocycles which may contain nitrogen, oxygen or sulphur as heteroatoms, for example tetrahydrofuran, tetrahydrofuranone, γ-butyrolactone, α-pyran, γ-pyran, dioxolane, tetrahydropyran, dioxane, dihydrothiophene, thiolane, dithiolane, pyrroline, pyrrolidine, pyrazoline, pyrazolidine, imidazoline, imidazolidine, tetrazole, piperidine, pyridazine, pyrimidine, pyrazine, piperazine, triazine, tetrazine, morpholine, thiomorpholine, diazepan, oxazine, tetrahydro-oxazinyl, isothiazole and pyrazolidine, preferably pyrazolyl, pyrrolidinyl, piperidinyl, piperazinyl or tetrahydro-oxazinyl, while the heterocyclic group may optionally be substituted.

The compounds of the above general formula (I) which contain a group that can be cleaved in-vivo are so-called prodrugs, and compounds of general formula I which contain two groups that can be cleaved in-vivo are so-called double prodrugs.

By a group which can be converted in-vivo into a carboxy group is meant for example an ester of formula —$CO_2R^{11}$, where $R^{11}$ denotes hydroxymethyl, alkenyl, alkynyl, aryl, heteroaryl, cycloalkenyl, hetero-cycloalkyl, $C_1$-$C_3$-alkoxycarbonyl, 1,3-dihydro-3-oxo-1-isobenzofuranol, —C(-alkyl)(-alkyl)-OC(O)-alkyl, —CHC(O)NH(-alkyl), —CHC(O)N(-alkyl)(-alkyl), -alkyl, preferably $C_1$-$C_6$-alkyl, particularly preferably methyl, ethyl, n-propyl, isopropyl, n-butyl, n-pentyl or n-hexyl, cycloalkyl, preferably $C_1$-$C_6$-cycloalkyl, particularly preferably cyclohexyl, —($C_1$-$C_3$-alkyl)-aryl, preferably ($C_1$-$C_3$-alkyl)-phenyl, particularly preferably benzyl, —CHC(O)N(-alkyl)(-alkyl), preferably —CHC(O)N(—$C_1$-$C_3$-alkyl)(—$C_1$-$C_3$-alkyl), particularly preferably —CHC(O)N($CH_3$)$_2$, —CH(-alkyl)OC(O)-alkyl, preferably —CH(—$CH_3$)OC(O) (—$C_1$-$C_6$-alkyl), particularly preferably —CH(—$CH_3$)OC (O)-methyl, —CH(—$CH_3$)OC(O)-ethyl, —CH(—$CH_3$)OC (O)-n-propyl, —CH(—$CH_3$)OC(O)-n-butyl or —CH(—$CH_3$)OC(O)-t-butyl, or —$CH_2$OC(O)-alkyl, preferably —$CH_2$OC(O)(—$C_1$-$C_6$-alkyl), particularly preferably —$CH_2$OC(O)-methyl, —$CH_2$OC(O)-ethyl, —$CH_2$OC(O)-n-propyl, —$CH_2$OC(O)-n-butyl or —$CH_2$OC(O)-t-butyl.

By a group which can be converted in-vivo into a sulphonamide or amino group is meant for example one of the following groups:

—OH, -formyl, —C(O)-alkyl, —C(O)-aryl, —C(O)-heteroaryl, —$CH_2$OC(O)-alkyl,

—CH(-alkyl)OC(O)-alkyl, —C(-alkyl)(-alkyl)OC(O)-alkyl,

—$CO_2$-alkyl, preferably $C_1$-$C_9$-alkoxy-carbonyl, particularly preferably methoxycarbonyl, ethoxycarbonyl, n-propyloxycarbonyl, isopropyloxycarbonyl, n-butyloxycarbonyl, n-pentyloxycarbonyl, n-hexyloxycarbonyl, cyclohexyloxycarbonyl, n-heptyloxycarbonyl, n-octyloxycarbonyl or n-nonyloxycarbonyl, —$CO_2$(—$C_1$-$C_3$-alkyl)-aryl, preferably —$CO_2$(—$C_1$-$C_3$-alkyl)-phenyl, particularly preferably benzyloxycarbonyl, —C(O)-aryl, preferably benzoyl,
—C(O)-heteroaryl, preferably pyridinoyl or nicotinoyl or
—C(O)-alkyl, preferably —C(O)(—$C_1$-$C_6$-alkyl), particularly preferably 2-methylsulphonyl-ethoxycarbonyl, 2-(2-ethoxy)-ethoxycarbonyl.

Halogen generally denotes fluorine, chlorine, bromine or iodine, preferably chlorine or fluorine, particularly preferably fluorine.

The compounds according to the invention may be in the form of the individual optical isomers, mixtures of the individual enantiomers, diastereomers or racemates, prodrugs, double prodrugs and in the form of the tautomers, salts, solvates and hydrates as well as in the form of the free bases or the corresponding acid addition salts with pharmacologically acceptable acids—such as for example acid addition salts with hydrohalic acids, for example hydrochloric or hydrobromic acid, or organic acids, such as for example oxalic, fumaric, diglycolic, formic, malic, benzoic, benzenesulphonic, camphorsulphonic, acetic, ethanesulphonic, glutamic, maleic, mandelic, lactic, phosphoric, nitric, sulphuric, succinic, para-toluenesulphonic, trifluoroacetic, tartaric, citric or methanesulphonic acid.

Moreover, if the new compounds of formula I thus obtained contain a carboxy group or another acid group, they may subsequently, if desired, be converted into the salts thereof with inorganic or organic bases, particularly for pharmaceutical use into the physiologically acceptable salts thereof. Suitable bases for this purpose include for example sodium hydroxide, potassium hydroxide, cyclohexylamine, ethanolamine, diethanolamine and triethanolamine.

Moreover the compounds of general formula I obtained may be resolved into their enantiomers and/or diastereomers.

Thus, for example, the compounds of general formula I obtained which occur as racemates may be separated by methods known per se (cf. Allinger N. L. and Eliel E. L. in "Topics in Stereochemistry", Vol. 6, Wiley Interscience, 1971) into their optical antipodes and compounds of general formula I with at least 2 asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The enantiomers are preferably separated by column separation on chiral phases or by recrystallisation from an optically active solvent or by reacting with an optically active substance which forms salts or derivatives such as e.g. esters or amides with the racemic compound, particularly acids and the activated derivatives or alcohols thereof, and separating the diastereomeric mixture of salts or derivatives thus obtained, e.g. on the basis of their differences in solubility, whilst the free antipodes may be released from the pure diastereomeric salts or derivatives by the action of suitable agents. Optically active acids in common use are e.g. the D- and L-forms of tartaric acid or dibenzoyltartaric acid, di-o-tolyl-tartaric acid, malic acid, mandelic acid, camphorsulphonic acid, glutamic acid, aspartic acid or quinic acid. An optically active alcohol may be, for example, (+) or (−)-menthol and an optically active acyl group in amides, for example, may be a (+)- or (−)-menthyloxycarbonyl.

As has been found, the compounds of general formula (I) are characterised by their great versatility in the therapeutic field. Particular mention should be made of those applications in which the effects of beta-3-agonists, particularly selective beta-3-agonists play a part.

Such diseases include for example:

atherosclerosis, cholangitis, gall bladder disease, chronic cystitis, chronic bladder inflammation; chronic prostatitis, cystospasm, depression, duodenal ulcer, duodenitis, dysmenorrhoea; increased intraocular pressure and glaucoma, enteritis, oesophagitis, gastric ulcer, gastritis, gastrointestinal disorders caused by contraction(s) of the smooth muscle, gastrointestinal disorders incl. gastric ulcer; gastrointestinal ulceration, gastrointestinal ulcers, glaucoma, glucosuria, hyperanakinesia, hypercholesterolaemia, hyperglycaemia, hyperlipaemia, arterial hypertension, hypertriglyceridaemia, insulin resistance, intestinal ulceration or small bowel ulcers (incl. inflammatory bowel diseases, ulcerative colitis, Crohn's disease and proctitis=inflammation of the rectum), irritable colon and other diseases with decreased intestinal motility, depression, melancholy, pollacisuria, frequent urinary urgency, nervous neurogenic inflammation, neurogenic bladder dysfunction, neurogenic inflammation of the respiratory tract, neuropathic bladder dysfunction, nycturia, non-specific diarrhoea, dumping syndrome, obesity, fatness, pancreatitis, inflammation of the pancreas, stomach ulcers, prostate diseases such as benign prostatic hyperplasia, enlarged prostate, spasm, cramp, type 2 diabetes mellitus, irritable bladder or concrement of the lower urinary tract.

The following may also be mentioned: urge incontinence, stress incontinence, mixed incontinence, overactive bladder (OAB) in the forms of wet OAB or dry OAB, OAB with imperative need to urinate, with or without urge incontinence, with or without increased frequency of urination, with or without nocturnal urination, dysuria, nycturia, pollacisuria, build-up of residual urine. Of these indications, OAB with increased frequency of urination, with or without urge incontinence, with or without nocturnal urination, is preferred.

The compounds may also be used in cases of pain in the prostate or of the lower urogenital tract. The diseases in question include benign prostatic hyperplasiam (BPH), prostatitis, particularly chronic abacterial prostatitis, of neurogenic, muscular or bacterial origin, chronic pain syndrome of the pelvis, pelvic myoneuropathy, prostatodynia, LUTS (lower urinary tract symptoms), obstructive bladder emptying disorders (BOO) and/or prostatopathy.

The use according to the invention is directed not only to causative treatment of the above indications, but also to the treatment of the accompanying symptoms, particularly any related pain or problems of urine release, pain and discomfort in the region of the prostate or the lower urinary tract including the penis, pain during erection or ejaculation, pain on defecation, erectile disorders.

The compounds according to the invention are also suitable for the treatment of neurodegenerative diseases such as e.g. Alzheimer's-type dementia (Alzheimer's disease), vascular dementia, Parkinson's dementia (Parkinson's disease), Huntington's disease, dystonia or degenerative ataxia.

The beta-3 agonists according to the invention are particularly suitable for the treatment of obesity, insulin resistance, type 2 diabetes mellitus, urinary incontinence, irritable colon and other diseases with decreased intestinal motility or depression, particularly for the treatment of diabetes and obesity.

The activity of the beta-3 agonists can be determined for example in a lipolysis test. The test procedure may be carried out as follows:

Adipocytes were isolated from fatty tissue ex vivo by modifying a method according to Rodbell (Rodbell, M. Metabolism of isolated fat cells. I. Effects of hormones on glucose metabolism and lipolysis. *J Biol Chem* 239: 375-380.1964). The excised fatty tissue was cut into small pieces and mixed with 1 mg/ml collagenase in Krebs Ringer Buffer (KRB) containing 6 mM glucose and 2% albumin by gently shaking for 30-40 min at 37° C. The cells were filtered through a gauze, washed twice with KRB and in each case 50-150 g were centrifuged for 5 min. 10 µl of the centrifuged adipocytes were incubated with 90 µl of a compound according to the invention (agonist) at concentrations of between $10^{-15}$ to $10^{-4}$ M. The agonists were incubated over 40 min at 37° C. A varying release of glycerol into the medium indicated that the fat cell lipolysis had altered as a result of the addition of the agonist. Released glycerol was detected enzymatically with a Sigma kit (triglyceride (GPO Trinder) Reagent A; Cat. #337-40A), as described below.

Glycerol is phosphorylated by ATP via glycerol kinase. The resulting glycerol-1-phosphate is oxidised by glycerol-phosphate oxidase to form dihydroxyacetone phosphate and hydrogen peroxide. Then a quinonimine dye is produced by the peroxidase-catalysed coupling of sodium-N-ethyl-N-(3-sulphopropyl)m-ansidine and 4-aminoantipyrine. The dye has an absorption peak at 540 nm. The absorption is directly proportional to the glycerol concentration in the samples.

The new compounds may be used for the prevention or short-term or long-term treatment of the above-mentioned diseases, and may also be used in conjunction with other active substances used for the same indications. These include, for example, antidiabetics, such as metformin, sulphonylureas (e.g. glibenclamid, tolbutamide, glimepiride), nateglinide, repaglinide, thiazolidinedione (e.g. rosiglitazone, pioglitazone), PPAR-gamma agonists (e.g. GI 262570), alpha-gluco-sidase inhibitors (e.g. acarbose, voglibose), alpha2 antagonists, insulin and insulin analogues, GLP-1 and GLP-1 analogues (e.g. exendin-4) or amylin. Also, inhibitors of protein tyrosine phosphatase 1, substances which influence deregulated glucose production in the liver, such as e.g. inhibitors of glucose-6-phosphatase, or fructose-1,6-bisphosphatase, glycogen phosphorylase, glucagon receptor antagonists and inhibitors of phosphoenol pyruvate carboxykinase, glycogen synthase kinase or pyruvate dehydrokinase, lipid lowering agents, such as HMG-CoA-reductase inhibitors (e.g. simvastatin, atorvastatin), fibrates (e.g. bezafibrate, fenofibrate), nicotinic acid and its derivatives, cholesterol absorption inhibitors such as for example ezetimibe, bile acid-binding substances such as for example cholestyramine, HDL-raising compounds such as for example inhibitors of CETP or regulators of ABC1 or active substances for the treatment of obesity, such as e.g. sibutramine or tetrahydrolipostatin.

In particular, they may also be combined with drugs for treating high blood pressure such as e.g. AII antagonists or ACE inhibitors, diuretics, β-blockers, and other modulators of the adrenergic system or combinations thereof. In addition, combinations with stimulators of the adrenergic system via alpha 1 and alpha 2 and also beta 1, beta 2 and beta 3 receptors are particularly suitable.

The compounds of general formula (I) may be used on their own or in conjunction with other active substances according to the invention, optionally also in conjunction with other pharmacologically active substances. Suitable preparations include for example tablets, capsules, suppositories, solutions, particularly solutions for injection (s.c., i.v., i.m.) and infusion, elixirs, emulsions or dispersible powders. The content of the pharmaceutically active compound(s) should be in the range from 0.1 to 90 wt. %, preferably 0.5 to 50 wt. % of the composition as a whole, i.e. in amounts which are sufficient to achieve the dosage range specified below. The specified doses may be taken several times a day, if necessary.

Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number or layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection and infusion are prepared in the usual way, e.g. with the addition of isotonic agents, preservatives such as p-hydroxybenzoates, or stabilisers such as alkali metal salts of ethylenediamine tetraacetic acid, optionally using emulsifiers and/or dispersants, whilst if water is used as the diluent, for example, optionally organic solvents may optionally be used as solvating agents or dissolving aids, and transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

The preparations are administered by the usual methods, preferably by oral or transdermal route, preferably oral. For oral administration the tablets may, of course contain, apart from the above-mentioned carriers, additives such as sodium citrate, calcium carbonate and dicalcium phosphate together with various added substances such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

For parenteral use, solutions of the active substances with suitable liquid carriers may be used.

The dosage for intravenous use is from 1-1000 mg per hour, preferably between 5 and 500 mg per hour.

However, it may sometimes be necessary to depart from the amounts specified, depending on the body weight, the route of administration, the individual response to the drug, the nature of its formulation and the time or interval over which the drug is administered. Thus, in some cases it may be sufficient to use less than the minimum dose given above, whereas in other cases the upper limit may have to be exceeded. When administering large amounts it may be advisable to divide them up into a number of smaller doses spread over the day.

The formulation Examples which follow illustrate the present invention without restricting its scope:

Examples Of Pharmaceutical Formulations

| A) Tablets | per tablet |
|---|---|
| active substance | 100 mg |
| lactose | 140 mg |
| corn starch | 240 mg |
| polyvinylpyrrolidone | 15 mg |
| magnesium stearate | 5 mg |
| | 500 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

| B) Tablets | per tablet |
|---|---|
| active substance | 80 mg |
| lactose | 55 mg |
| corn starch | 190 mg |
| microcrystalline cellulose | 35 mg |
| polyvinylpyrrolidone | 15 mg |
| sodium-carboxymethyl starch | 23 mg |
| magnesium stearate | 2 mg |
| | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodiumcarboxymethyl starch and the magnesium stearate are added and mixed in and the mixture is compressed to form tablets of a suitable size.

| C) Ampoule solution | |
|---|---|
| active substance | 50 mg |
| sodium chloride | 50 mg |
| water for inj. | 5 ml |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion. The ampoules contain 5 mg, 25 mg and 50 mg of active substance.

The following Examples illustrate the present invention without restricting its scope:

Abbreviations Used:

ammonia 32% ammonia solution in water

DBU 1,8-diazabicyclo[5.4.0]undec-7-ene

DC thin layer chromatography

DCM dichloromethane

DIPEA N-ethyl-diisopropylamine

DMAP 4-dimethylamino-pyridine

DMF N,N-dimethylformamide

DMPU 1,3-dimethyl-3,4,5,6-tetrahydro-2(1H)-pyrimidinone

EDCI N-(3-dimethylaminopropyl)-N'-ethyl-carbodiimide hydrochloride

HOBt hydroxybenzotriazole-hydrate

KG silica gel

MeOH methanol $NH_3$ 32% ammonia solution in water $NH_4OH$ 32% ammonia solution in water RT ambient temperature TBTU O-(benzotriazol-1-yl)-N,N,N',N'-tetramethyluronium tetrafluoroborate TFA trifluoroacetic acid THF tetrahydrofuran HPLC methods:

Method 1:

Retention times were determined using an apparatus made by Agilent, type 1100 (quaternary pump, diode array detector, LC-MSD) fitted with a Merck Cromolith Speed ROD column (RP18e, 50×4.6 mm). For elution mixtures of acetonitrile and water, in each case modified with 0.1% formic acid, were used at a flow rate of 1.5 ml/min with the following gradient pattern:

| time [minutes] | vol % acetonitrile |
|---|---|
| 0.0 | 10 |
| 4.5 | 90 |
| 5.0 | 90 |
| 5.5 | 10 |

The enantiomeric excess (% ee) was determined on a type 1100 apparatus made by Agilent under the following conditions:

Method 2:

DAICEL AS-H column (150×4.6 mm); elution with hexane/isopropanol (80:20) at a flow rate of 1 ml/min, a temperature of 20° C. and detection at 254 nM.

Method 3:

Astec Chirobiotic T column (250×4.6 mm); elution with acetonitrile/methanol/glacial acetic acid/triethylamine (15:85:0.05:0.05) at a flow rate of 2 ml/min, a temperature of 35° C. and detection at 300 nM.

Preparation of the Starting Compounds Component I N-[3-(2-ethoxy-2-hydroxyacetyl)-phenyl]-benzene-sulphonamide

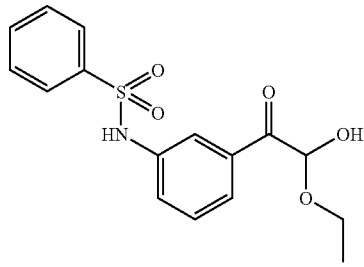

1 ml of water, 1 g activated charcoal and 2.66 g (24 mmol) selenium dioxide are added to a solution of 1.65 g (6 mmol) N-(3-acetyl-phenyl)-benzenesulphonamide in 10 ml dioxane. The reaction mixture is stirred for 4 days at 80° C. and then concentrated by evaporation in the rotary evaporator. The residue is dissolved in 30 ml of ethanol and refluxed for 4 hours. Then the reaction mixture is concentrated by evaporation in the rotary evaporator. The residue is dissolved in 100 ml of ethyl acetate, washed several times with 30 ml saturated, aqueous sodium hydrogen carbonate solution, dried on sodium sulphate and again concentrated by evaporation in the rotary evaporator. The crude product thus obtained as a yellow solid is reacted further without any further purification.

Yield: 0.917 g crude product (46% of theory)
$C_{16}H_{17}NO_5S$ (335.38)

Component II

N—[(R)-3-oxiranyl-phenyl]-dibenzenesulphonamide

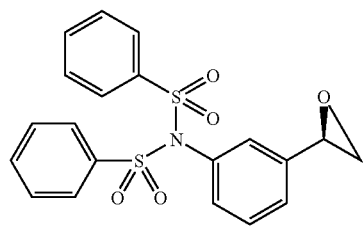

a. N-(3-acetyl-phenyl)-dibenzenesulphonamide 2.75 g (10 mmol) N-(3-acetyl-phenyl)-benzenesulphonamide are dissolved in 50 ml acetonitrile and combined with 3.3 ml (24 mmol) triethylamine. With vigorous stirring 3.89 g (22 mmol) benzenesulphonic acid chloride are added dropwise over a period of 10 minutes at ambient temperature. The reaction mixture is then stirred for 20 hours at ambient temperature and then concentrated by evaporation in the rotary evaporator. The residue is poured into ice water, whereupon a beige solid is precipitated. This precipitate is filtered off and recrystallised from ethyl acetate.

Yield: 3.6 g (87% of theory)
$C_{20}H_{17}NO_5S_2$ (415.49)
Mass spectrum: $(M+NH_4)^+=433$
$R_f=0.44$ (silica gel; toluene/ethyl acetate=9:1)

b. N-[3-(2-chloro-acetyl)-phenyl]-dibenzenesulphonamide 2.1 ml (26 mmol) sulphuryl chloride are added dropwise to 3.6 g (8.66 mmol) N-(3-acetyl-phenyl)-dibenzenesulphonamide in 70 ml DCM and 2.11 ml (52 mmol) methanol at 0° C. with vigorous stirring over a period of 20 min. The reaction mixture is refluxed for 2.5 hours and then stirred for 18 hours at ambient temperature. Then the reaction solution is washed with water, saturated, aqueous sodium hydrogen carbonate solution and saturated, aqueous sodium chloride solution. The organic phase is separated off, dried on magnesium sulphate and concentrated by evaporation in the rotary evaporator. The residue is recrystallised from toluene to obtain a colourless solid.

Yield: 2.55 g (65% of theory)
$C_{20}H_{16}ClNO_5S_2$ (449.93)
Mass spectrum: $(M+NH_4)^+=459, 457$
$R_f=0.56$ (silica gel; toluene/ethyl acetate=9:1)

c. N—[(R)-3-oxiranyl-phenyl]-dibenzenesulphonamide 7.84 g (24.4 mmol) (−)-B-chloro-diisopinocampheylboran dissolved in 15 ml THF are added dropwise at −30° C. over a period of 60 minutes to a solution of 5.00 g (11.1 mmol) N-[3-(2-chloro-acetyl)-phenyl]-dibenzenesulphonamide in 70 ml THF. After one hour another 2.00 g (6.24 mmol) (−)-B-chloro-diisopinocampheylborane dissolved in 5 ml THF are added dropwise at −30° C. The mixture is stirred for 14 hours at this temperature and the reaction solution is then poured into a mixture of ice water and saturated sodium hydrogen carbonate solution. The mixture is extracted with ethyl acetate, the combined organic phases are washed and dried on magnesium sulphate. Then the mixture is evaporated to dryness. The residue is chromatographed on silica gel (toluene/ethyl acetate=97.5:2.5→90:10). The intermediate product is triturated with diisopropylether, suction filtered and dried. The solid is dissolved in 30 ml DMF and combined with 8.33 ml 4 N lithium hydroxide solution at −5° C. with stirring within 15 minutes. Meanwhile 3 ml DMF and 2 ml of water are added to improve the stirrability. After 25 minutes the reaction mixture is acidified at −5° C. with glacial acetic acid and diluted with water. The solid thus precipitated is suction filtered, washed several times with ice water and dried. (The product may be obtained in racemic form by reacting of N-[3-(2-chloro-acetyl)-phenyl]-dibenzenesulphonamide with borane-THF complex (1M in THF) and then with 4 M lithium hydroxide.)

Yield: 3.65 g (79% of theory)
$C_{20}H_{17}NO_5S_2$ (415.49)
Mass spectrum: $(M+NH_4)^+=433$
$R_f$ value: 0.47 (silica gel; toluene/ethyl acetate=9:1)

Component III

1-(3-amino-3-methyl-butyl)-5-cyano-indole

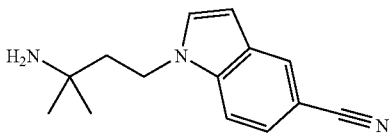

a. 1-(3-tert-butoxycarbonylamino-3-methyl-butyl)-5-cyano-indole

Under a nitrogen atmosphere 4.07 g (16.9 mmol) 5-cyanoindole are dissolved in 30 ml DMF, and 0.73 g (18.3 mmol) sodium hydride (60% dispersion in mineral oil) are added batchwise while cooling with ice and with stirring. Then the mixture is stirred for 30 minutes at ambient temperature. It is heated to 50° C., 0.41 g (1.1 mmol) tetrabutylammonium iodide are added and over a period of 5 hours a solution of N-tert-butoxycarbonyl-3-chloro-1,1-dimethyl-propylamine is added dropwise. Then the mixture is stirred for 18 hours at ambient temperature. Then the reaction solution is poured onto water and extracted with ethyl acetate. The organic phases are combined, dried on sodium sulphate and freed from the solvent in vacuo. The residue is chromatographed on silica gel (petroleum ether/ethyl acetate=100:0→70:30). The product fractions are combined and freed from the solvent in vacuo. The residue is dissolved in 5 ml of methanol and poured onto 50 ml hot water. The precipitate thus obtained is suction filtered and dried in vacuo and reacted further without any further purification.

Yield: 2.1 g crude product (38% of theory)
$C_{19}H_{25}N_3O_2$ (327.42)
Mass spectrum: $(M+H)^+=328$
$R_f=0.32$ (silica gel; petroleum ether/ethyl acetate=6:1)

b. 1-(3-amino-3-methyl-butyl)-5-cyano-indole-hydrotrifluoroacetate 2.0 g (6.1 mmol) 1-(3-tert-butoxycarbonylamino-3-methyl-butyl)-5-cyano-indole are dissolved in 15 ml DCM and 2.4 ml m-dimethoxybenzene and combined with 15 ml trifluoroacetic acid with stirring. The reaction solution is heated to 40° C. for 2 hours. Then the solvent is eliminated in vacuo and the residue is chromatographed on Varian Microsorb C18-reverse-phase [acetonitrile (0.1% TFA)/water (0.13% TFA)=10:90→100:0].

Yield: 2.74 g (80% of theory)
$C_{14}H_{17}N_3 \times C_2HF_3O_2$ (341.33)
Mass spectrum: $(M+H)^+=228$
$R_f=0.71$ (silica gel; DCM/methanol/$NH_4OH$=80:20:0.1)

Component IV methyl 1-(3-amino-3-methyl-butyl)-indole-5-carboxylate

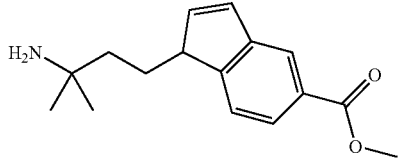

Prepared analogously to Component III by alkylation of methyl indole-5-carboxylate with N-tert-butoxycarbonyl-3-chloro-1,1-dimethyl-propylamine and subsequent cleaving of the acid protecting group.

Yield: 27% of theory
$C_{15}H_{20}N_2O_2$ (260.33)
Mass spectrum: $(M+H)^+=261$
$R_f=0.47$ (silica gel; DCM/methanol/$NH_4OH$=60:10:0.1)

Component V

1-(3-amino-3-methyl-butyl)-5-(methylsulphanyl)-indole-hydrochloride

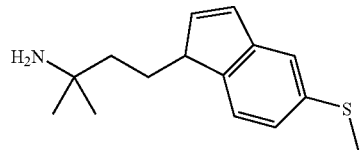

a. 1-(3-tert-butoxycarbonylamino-3-methyl-butyl)-5-(methylsulphanyl)-indole

Under a nitrogen atmosphere 500 mg (2.6 mmol) 5-(methylsulphanyl)-indole (Yang et al., Heterocycles, 1992, vol. 34, No. 6, page 1169-1175) are dissolved in 6 ml DMF and combined with 357 mg (3.2 mmol) potassium-tert-butoxide with stirring and cooling with ice. Then the mixture is stirred for 10 minutes at 0° C. 768 mg (2.9 mmol) N-tert-butoxycarbonyl-4,4-dimethyl-[1,2,3]oxathiazinane-2,2-dioxide (Component XI) are added. The mixture is then stirred for three hours at ambient temperature. Then the reaction solution is poured onto water and hydrochloric acid (1.2 mmol) and extracted with ethyl acetate. The organic phases are combined, dried on sodium sulphate and freed from the solvent in vacuo.

Yield: 1.0 g crude product (99% of theory)
$C_{19}H_{28}N_2O_2S$ (348.50)
Mass spectrum: $(M+H)^+=349$
$R_f=0.52$ (silica gel; petroleum ether/ethyl acetate=4:1)

b. 1-(3-amino-3-methyl-butyl)-5-(methylsulphanyl)-indole-hydrochloride 1.0 g (2.9 mmol) 1-(3-tert-butoxycarbonylamino-3-methyl-butyl)-5-(methylsulphanyl)-indole are dissolved in 5 ml of methanol at 0° C. and combined with 2.9 ml 4N hydrochloric acid (solution in dioxane) with stirring. Then the reaction mixture is stirred for 18 hours at RT. The solvent is eliminated in vacuo and the residue is chromatographed on Varian Microsorb C18-reverse-phase [acetonitrile (0.1% TFA)/water (0.13% TFA)=10:90→100:0].

Yield: 500 mg (61% of theory)
$C_{14}H_{20}N_2S \times HCl$ (284.85)
Mass spectrum: $(M+H)^+=249$
retention time (Method 1): 2.39 min

TABLE 1

Prepared analogously to Component III or V by alkylation of the corresponding indole with N-tert-butoxycarbonyl-3-chloro-1,1-dimethyl-propylamine or N-tert-butoxycarbonyl-4,4-dimethyl-[1,2,3]oxathiazinane-2,2-dioxide (Component XI) and subsequent cleaving of the acid protecting group.

| starting-compound | anologous starting compound | structure | name | DC $R_f$ | ESI $(M + H)^+$ | HPLC retention time (min.) | formula | yield | molar mass |
|---|---|---|---|---|---|---|---|---|---|
| VI.1 | III | 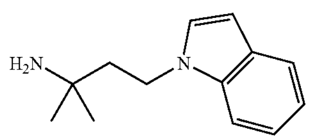 | 3-(indol-1-yl)-1,1-dimethyl-propylamine | 0.25 KG DCM/MeOH/ $NH_3$ 90/10/0.1 | 203 | | $C_{13}H_{18}N_2$ | 76% | 202.3 |
| VI.2 | III | 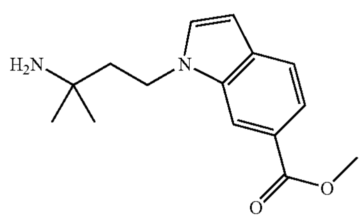 | methyl 1-(3-amino-3-methyl-butyl)-1H-indole-6-carboxylate | 0.27 KG DCM/MeOH/ $NH_3$ 90/10/0.1 | 261 | | $C_{15}H_{20}N_2O_2$ | 83% | 260.34 |
| VI.3 | III | 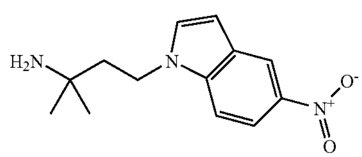 | 1,1-dimethyl-3-(5-nitro-indol-1-yl)-propylamine | | 248 | 2.16 meth. 1 | $C_{13}H_{17}N_3O_2$ | 96% | 247.3 |
| VI.4 | V | 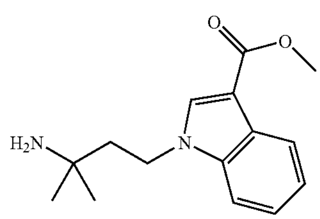 | methyl 1-(3-amino-3-methyl-butyl)-1H-indole-3-carboxylate | | 261 | 2.21 meth. 1 | $C_{15}H_{20}N_2O_2$ | 86% | 260.34 |
| VI.5 | V | 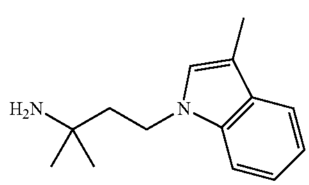 | 1,1-dimethyl-2-(3-methyl-indol-1-yl)-propylamine | 0.41 KG DCM/MeOH/ $NH_3$ 90/10/0.1 | 217 | | $C_{14}H_{20}N_2$ | 89% | 216.33 |
| VI.6 | V | 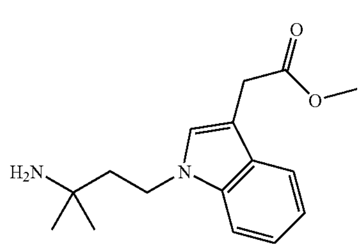 | methyl [1-(3-amino-3-methyl-butyl)-1H-indol-3-yl]-acetate | 0.40 KG DCM/MeOH/ $NH_3$ 90/10/0.1 | 275 | | $C_{16}H_{22}N_2O_2$ | 68% | 274.37 |

Component VII

N-benzenesulphonyl-N-(3-{(R)-2-[3-(5-formyl-indol-1-yl)-1,1-dimethyl-propylamino]-1-hydroxy-ethyl}-phenyl)-benzenesulphonamide

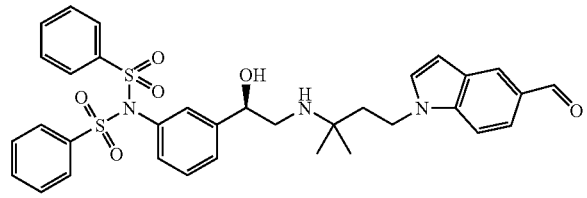

a. 1-(3-tert-butoxycarbonylamino-3-methyl-butyl)-1H-indole-5-carbaldehyde

Prepared analogously to Component V(a) by alkylation of indole-5-carbaldehyde with N-tert-butoxycarbonyl-4,4-dimethyl-[1,2,3]oxathiazinane-2,2-dioxide (Component XI).
Yield: 100% of theory
$C_{19}H_{26}N_2O_3$ (330.42)
Mass spectrum: $(M+H)^+=331$
$R_f=0.30$ (silica gel; petroleum ether/ethyl acetate=8:2)

b. 1-(3-amino-3-methyl-butyl)-1H-indole-5-carbaldehyde

A suspension of 1-(3-tert-butoxycarbonylamino-3-methyl-butyl)-1H-indole-5-carbaldehyde (3.5 g; 10.6 mmol) in 18 ml of water is heated for 19 hours at 150° C. in the microwave. Then the reaction mixture is extracted with DCM, dried on magnesium sulphate and freed from the solvent in vacuo. The residue is chromatographed on silica gel (DCM/methanol=1:1).
Yield: 68% of theory
$C_{14}H_{18}N_2O$ (230.31)
Mass spectrum: $(M+H)^+=231$
$R_f=0.24$ (silica gel; DCM/methanol=1:1)

c. N-benzenesulphonyl-N-(3-{(R)-2-[3-(5-formyl-indol-1-yl)-1,1-dimethyl-propylamino]-1-hydroxy-ethyl}-phenyl)-benzenesulphonamide A mixture of 1.01 g (2.43 mmol) N—[(R)-3-oxiranyl-phenyl]-dibenzenesulphonamide (Component II) and 700 mg (3.04 mmol) 1-(3-amino-3-methyl-butyl)-1H-indole-6-carbaldehyde is heated to 120° C. in 3 ml ethyleneglycol for 2.5 hours. Then the reaction mixture is chromatographed on silica gel (DCM/methanol=100:0→95:5).
Yield: 570 mg (36% of theory)
$C_{34}H_{35}N_3O_6S_2$ (645.79)
Mass spectrum: $(M+H)^+=646$
$R_f=0.53$ (silica gel; DCM/methanol=9:1)

Component VIII

1-[1-9'-(3-amino-3-methyl-butyl)-1H-indol-5-yl]-2,2,2-trifluoro-ethanone

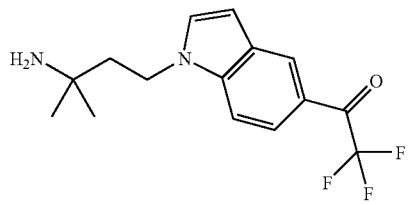

a. 2,2,2-trifluoro-1-(1H-indol-5-yl)-ethanone

At 0° C. and under argon a solution of 5-bromoindole (5.0 g, 25 mmol) in 25 ml THF is added dropwise to a suspension of potassium hydride (3.4 g of a 30% suspension in mineral oil, 25 mmol) in 50 ml THF. After 20 minutes stirring at 0° C. the mixture is cooled to −78° C. and over a period of 10 minutes a solution of tert-butyllithium (30 ml of a 1.7M solution in pentane, 51 mmol) is added dropwise. After 20 minutes stirring at −78° C. trifluoroacetic anhydride (7.2 ml, 51 mmol) is added and the mixture is stirred for 30 minutes at −78° C. Then ammonium chloride (20 ml saturated solution) is added and the mixture is slowly heated to RT. The reaction mixture is extracted with diethyl ether. The organic phases are combined, washed with saturated aqueous sodium chloride solution, dried on sodium sulphate and freed from the solvent in vacuo. The residue is chromatographed on silica gel (ethyl acetate/hexane=1:2).
Yield: 45% of theory
$C_{10}H_6F_3NO$ (213.16)
Mass spectrum: $(M+H)^+=214$
$R_f=0.35$ (silica gel; ethyl acetate/hexane=1:2)

b. 1-[1-(3-amino-3-methyl-butyl)-1H-indol-5-yl]-2,2,2-trifluoro-ethanone

Prepared analogously to Component V by alkylation of 2,2,2-trifluoro-1-(1H-indol-5-yl)-ethanone with N-tert-butoxycarbonyl-4,4-dimethyl-[1,2,3]oxathiazinane-2,2-dioxide (Component XI) and subsequent cleaving of the acid protecting group.
Yield: 24% of theory
$C_{20}H_{25}F_3N_2O_3$ (398.42)
Mass spectrum: $(M+H)^+=399$
IR $(cm^{-1})$: 2953, 1702, 1610, 1433, 1310, 1250, 1192, 751

Component IX

3-[1-(3-amino-3-methyl-butyl)-1H-indol-5-yl]-2H-[1,2,4]oxadiazol-5-one-hydrotrifluoroacetate

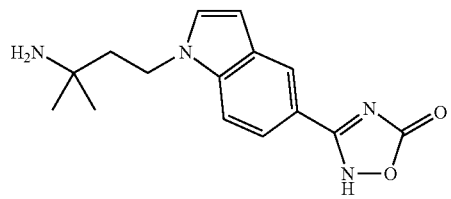

a. 1-(3-amino-3-methyl-butyl)-N-hydroxy-1H-indole-5-carboxamidine-hydrotrifluoroacetate Hydroxylamine (6 ml, 86 mmol) is added to a solution of 1-(3-amino-3-methyl-butyl)-5-cyano-indole-hydrotrifluoroacetate (Component III; 1.0 g, 2.93 mmol) in 50 ml of ethanol. The reaction mixture is refluxed for 5 hours and then freed from the solvent in vacuo.
Yield: 80% of theory
$C_{14}H_{20}N_4O \times CF_3CO_2H$ (374.36); $C_{14}H_{20}N_4O$ (260.34)
Mass spectrum: $(M+H)^+=260$
$R_f=0.22$ (DCM/methanol/ammonia=80:20:0.1)

b. 3-[1-(3-amino-3-methyl-butyl)-1H-indol-5-yl]-2H-[1,2,4]oxadiazol-5-one-hydrotrifluoroacetate Carbonyldiimidazole (357 mg, 2.24 mmol) is added to a solution of 1-(3-amino-3-methyl-butyl)-N-hydroxy-1H-indole-5-carboxamidine-hydrotrifluoroacetate (550 mg, 1.47 mmol) in 50 ml THF. The reaction mixture is stirred for two hours at 60° C. and then freed from the solvent in vacuo. The residue is chromatographed on Varian Microsorb C18-reverse-phase [acetonitrile (0.1% TFA)/water (0.13% TFA)=10:90→100:0].

Yield: 20% of theory
$C_{15}H_{18}N_4O_2 * CF_3CO_2H$ (400.35); $C_{15}H_{18}N_4O_2$ (286.34)
Mass spectrum: $(M+H)^+=287$
$R_f=0.08$ (DCM/methanol/ammonia=80:20:0.1)

Component X

1-[1-(3-amino-3-methyl-butyl)-1H-indol-5-yl]-2-methanesulphonyl-ethanone

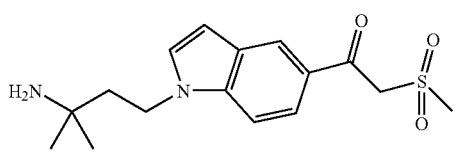

Potassium tert. butoxide (741 mg, 6.62 mmol) is added in two batches to a solution of dimethylsulphone (661 mg, 7.03 mmol) in 5 ml DMSO. After 10 minutes stirring at RT a solution of methyl 1-(3-amino-3-methyl-butyl)-indole-5-carboxylate (Component IV) (520 mg, 2.00 mmol) in 2 ml DMSO is added dropwise over 10 minutes. The reaction mixture is stirred for 16 hours at 70° C., acidified with TFA while cooling with ice and chromatographed on Microsorb C18-reverse-phase [acetonitrile (0.1% TFA)/water (0.13% TFA)=10:90→100:0]. Then the residue is chromatographed again on silica gel (DCM/methanol/ammonia=90:9:1).

Yield: 90 mg (14% of theory)
$C_{16}H_{22}N_2O_3S$ (322.42)
Mass spectrum: $(M+H)^+=323$
$R_f=0.40$ (DCM/methanol/ammonia=90:9:1)

Component XI

Preparation of the Compound of Formula (IIIb)

N-tert-butoxycarbonyl-4,4-dimethyl-[1,2,3]oxathiazinane-2,2-dioxide

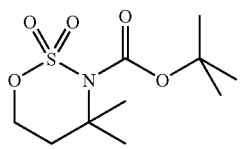

a. tert-butyl (3-hydroxy-1,1-dimethylpropyl)-carbamidate

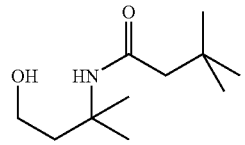

3-amino-3-methylbutan-1-ol (200.0 g, 1.94 mol) is dissolved in ethyl acetate (0.75 l) and within one hour combined with a solution of di-tert-butyl-dicarbonate (435.0 g, 1.99 mol) in ethyl acetate (0.75 l). After the addition has ended the reaction mixture is stirred for another 30 min. After elimination of the solvent the title compound is obtained, which is used in the next step without further purification.

Yield: 412.5 g
$^1$H-NMR (DMSO, 400 MHz): 1.19 (s, 9H); 1.36 (s, 6H); 1.68-1.74 (m, 2H); 3.42-3.50 (m, 2H); 4.39 (t, J=4.8, 1H); 6.36 (br s, 1H).

Alternatively tert-butyl (3-hydroxy-1,1-dimethylpropyl)-carbamidate may also be prepared using the methods described for example in J. of Labell. Compounds & Radioph. 2001, 44(4), 265-275 or der WO 03/037327, p. 82/83.

b. N-tert-butoxycarbonyl-4,4-dimethyl-[1,2,3]oxathiazinane-2-oxide

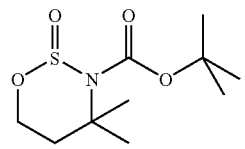

Thionyl chloride (171.0 ml, 2.23 mol) is dissolved in acetonitrile (0.6 l). The solution is cooled to −45° C. and within 20 min combined with a solution of unpurified tert-butyl (3-hydroxy-1,1-dimethylpropyl)-carbamidate (from Step a) (200.0 g, 0.93 mol) in acetonitrile (0.7 l), while the internal temperature is maintained at below −40° C. Then dimethylaminopyridine (11.0 g, 0.09 mol) is added, followed by the slow addition of pyridine (378.0 m, 4.70 mol) over 2 hours at −45° C. The mixture is stirred for another hour at this temperature, then ethyl acetate (2.5 l) is added. The suspension is stirred for 30 min, during which time the temperature rises to −15° C. The precipitate is filtered off and washed with ethyl acetate (2×0.1 l). The combined filtrates are added to a saturated aqueous solution of disodium hydrogen phosphate (0.8 l) and the two-phase mixture is stirred for one hour. The organic layer is washed first of all with 1 M hydrochloric acid (1.0 l) and then with saturated saline solution (1.0 l). After drying on $Na_2SO_4$ and elimination of the solvent 204.3 g crude product (containing approx. 60 wt. % of the title compound) are obtained. This crude product is used in the next step without further purification.

Alternatively dichloromethane, dimethoxyethane, acetone, methylethylketone, ethylacetate, DMF, N-methylpyrrolidone or DMPU may also be used as solvent instead of acetonitrile, for example. The use of acetonitrile is preferred. As base, instead of pyridine, other aromatic bases such as imidazole or N-methylimidazole or a combination of these bases with aliphatic bases, for example pyridine/triethylamine (TEA) may be used. The addition of dimethylaminopyridine (DMAP) is optional; step b may also be carried out without the addition of DMAP.

c. N-tert-butoxycarbonyl-4,4-dimethyl-[1,2,3]oxathiazinane-2,2-dioxide

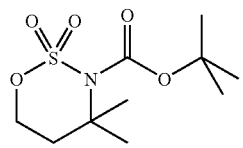

A solution of ruthenium(III)chloride hydrate (440 mg, 2.12 mmol, 0.003 equiv) and sodium metaperiodate (132.2 g, 0.62 mol) in water (1.5 l) is stirred for 45 min and added at a temperature of 20-25° C. over a period of 35 min to a suspension of the crude product of Step b (140 g) in a mixture of acetonitrile (0.6 l) and saturated aqueous solution of disodium hydrogen phosphate (0.3 l). During the addition the pH of the suspension is kept between 6.9 and 7.3 by the continuous addition of additional saturated aqueous solution of disodium hydrogen phosphate (1.0 l). After the addition has ended the reaction mixture is stirred for 1 hour at 20° C., the pH is adjusted to 6.4 with 1 M hydrochloric acid and then stirring is continued for a further hour. The solid is collected by filtration, washed with water (3×100 ml) and lastly stirred for 2 hours with water (1.5 l). The crystals are isolated by filtration, washed with water (3×0.1 l) and dried at 50° C.

Yield: 87.4 g (51.3%, over two steps)

$^1$H-NMR (DMSO, 400 MHz): 1.45 (s, 9H); 1.52 (s, 6H); 2.27 (t, J=6.60 Hz, 2H); 4.68 (t, J=6.60 Hz, 2H).

The use of a buffered (disodium hydrogen phosphate) environment is optional, but is preferred. Possible alternatives to disodium hydrogen phosphate might be for example sodium phosphate, sodium and/or potassium bicarbonate, sodium and/or potassium carbonate or sodium and/or potassium hydroxide. Possible alternative ruthenium sources include for example ruthenium(VIII)tetroxide, ruthenium(IV)oxide, ruthenium(III)bromide, ruthenium(III)iodide (anhydrous or hydrate) and perruthenate (Ru(VII)). Instead of sodium metaperiodate, alternatively potassium permanganate or oxone might possibly be used.

Preparation of the End Products

Example 1

N-(3-{(R)-2-[3-(5-cyano-indol-1-yl)-1,1-dimethyl-propylamino]-1-hydroxy-ethyl}-phenyl)-benzene-sulphonamide

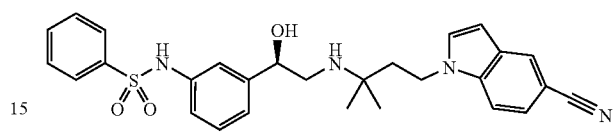

a. N-(3-{(R)-2-[3-(5-cyano-indol-1-yl)-1,1-dimethyl-propylamino]-1-hydroxy-ethyl}-phenyl)-dibenzene-sulphonamide A mixture of 822 mg (1.98 mmol) N—[(R)-3-oxiranyl-phenyl]-dibenzenesulphonamide (Component II) and 450 mg (1.98 mmol) 1-(3-amino-3-methyl-butyl)-5-cyano-indole (free base from Component III) is heated to 120° C. for 2 hours. Then the reaction mixture is chromatographed on silica gel (DCM/methanol=100:0→88:12).

Yield: 740 mg (58% of theory)
$C_{34}H_{34}N_4O_5S_2$ (642.79)
Mass spectrum: (M+H)$^+$=643
$R_f$=0.61 (silica gel; DCM/methanol=9:1)

b. N-(3-{(R)-2-[3-(5-cyano-indol-1-yl)-1,1-dimethyl-propylamino]-1-hydroxy-ethyl}-phenyl)-benzene-sulphonamide 700 mg (1.09 mmol) N-(3-{(R)-2-[3-(5-cyano-indol-1-yl)-1,1-dimethyl-propylamino]-1-hydroxy-ethyl}-phenyl)-dibenzenesulphonamide are dissolved in 10 ml of ethanol and combined with 10 ml 4N sodium hydroxide solution. The mixture is stirred for 5 hours at ambient temperature and then the reaction solution is neutralised with TFA. After elimination of the solvent in vacuo the residue is chromatographed on silica gel (DCM/methanol/NH$_4$OH=100:0:0→85:15:0.1).

Yield: 440 mg (80% of theory)
$C_{28}H_{30}N_4O_3S$ (502.63)
Mass spectrum: (M+H)$^+$=503
$R_f$=0.47 (silica gel; DCM/methanol/NH$_4$OH=90:10:0.1)

Example 2

N-[3-((R)-2-{1,1-dimethyl-3-[5-(tetrazol-5-yl)-indol-1-yl]-propylamino}-1-hydroxy-ethyl)-phenyl]-benzenesulphonamide

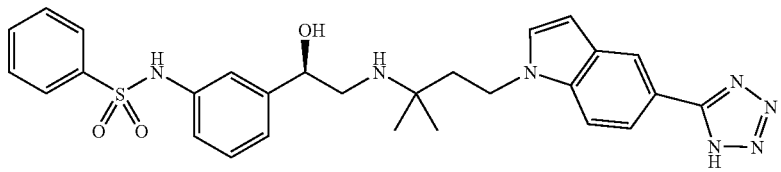

150 mg (0.30 mmol) N-(3-{(R)-2-[3-(5-cyano-indol-1-yl)-1,1-dimethyl-propylamino]-1-hydroxy-ethyl}-phenyl)-benzenesulphonamide (Example 1) are dissolved in 5 ml of toluene and combined with 98 μl (0.36 mmol) tributyltin azide. Then the reaction solution is refluxed for 18 hours. Another 164 μl (0.6 mmol) tributyltin azide are added. The mixture is refluxed for a further 36 hours. Then the solvent is eliminated in vacuo and the residue is chromatographed on silica gel (DCM/methanol/NH$_4$OH=100:0:0→70:30:0.3).

Yield: 102 mg (63% of theory)
C$_{28}$H$_{31}$N$_7$O$_3$S (545.66)
Mass spectrum: (M+H)$^+$=546
R$_f$=0.51 (silica gel; DCM/methanol/NH$_4$OH=80:20:0.1)

Example 3

Methyl 1-{3-[2-[3-(phenylsulphonylamino)-phenyl]-2-hydroxy-ethylamino]-3-methyl-butyl}-1H-indole-5-carboxylate

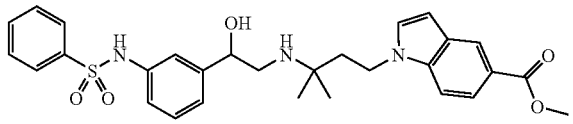

154 mg (0.46 mmol) N-[3-(2-ethoxy-2-hydroxyacetyl)-phenyl]-benzenesulphonamide (Component I) and 125 mg (0.48 mmol) methyl 1-(3-amino-3-methyl-butyl)-indole-5-carboxylate (Component IV) are dissolved in 10 ml of ethanol and combined with 4 drops of triethylamine. The reaction solution is heated to 80° C. for 17 hours. Then it is cooled to 0° C. and over a period of 2.5 hours 140 mg (3.7 mmol) sodium borohydride are added batchwise. The mixture is stirred for another hour at 0° C. and the reaction solution is then poured into a mixture of 20 ml of saturated aqueous potassium carbonate solution and 50 ml of ethyl acetate. After separation of the organic phase the aqueous phase is extracted with ethyl acetate. The combined organic phases are with washed saturated aqueous saline solution and dried on sodium sulphate. Then the solvent is eliminated in vacuo and the residue is chromatographed on silica gel (DCM/methanol=100:0:0→9:1).

Yield: 107 mg (44% of theory)
C$_{29}$H$_{33}$N$_3$O$_5$S (535.66)
Mass spectrum: (M+H)$^+$=536
R$_f$=0.39 (silica gel; DCM/methanol=9:1)

Example 4

1-{3-[2-[3-(phenylsulphonylamino)-phenyl]-2-hydroxy-ethylamino]-3-methyl-butyl}-1H-indole-5-carboxylic acid-hydrotrifluoroacetate

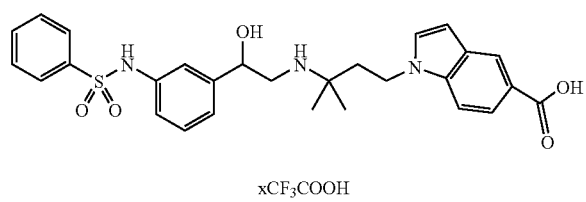

xCF$_3$COOH 80 mg (0.15 mmol) methyl 1-{3-[2-[3-(phenylsulphonylamino)-phenyl]-2-hydroxy-ethylamino]-3-methyl-butyl}-1H-indole-5-carboxylate (Example 3) are dissolved in 1 ml DMF and combined with 1 ml 2 N lithium hydroxide solution. The mixture is stirred for 2 days at ambient temperature. Then another 1 ml of 2 N lithium hydroxide solution and 100 mg (2.38 mol) lithium hydroxide monohydrate are added and the mixture is stirred for 5 hours at ambient temperature. Then the reaction solution is acidified with TFA and the solvent is eliminated in vacuo. The residue is chromatographed on Varian Microsorb C18-reverse-phase [acetonitrile (0.1% TFA)/water (0.13% TFA)=10:90->100:0].

Yield: 65 mg (69% of theory)
C$_{28}$H$_{31}$N$_3$O$_5$S×C$_2$HF$_3$O$_2$ (635.65)
Mass spectrum: (M+H)$^+$=522
R$_f$=0.35 (silica gel; DCM/methanol/glacial acetic acid=9:1:0.1)

Example 5

1-{3-[(R)-2-[3-(phenylsulphonylamino)-phenyl]-2-hydroxy-ethylamino]-3-methyl-butyl}-1H-indole-5-carboxylate methyl-hydrotrifluoroacetate

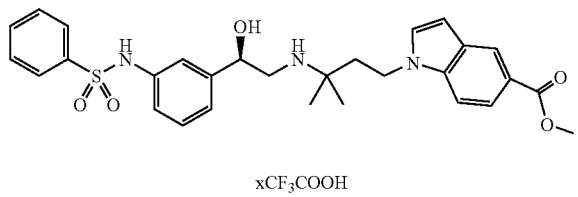

xCF$_3$COOH

Prepared analogously to Example 1 by reacting N—[(R)-3-oxiranyl-phenyl]-dibenzenesulphonamide (Component II) with methyl 1-(3-amino-3-methyl-butyl)-indole-5-carboxylate (Component IV), subsequent reaction with sodium hydroxide solution (1 hour) and acidification with TFA.

Yield: 55% of theory
C$_{29}$H$_{33}$N$_3$O$_5$S×C$_2$HF$_3$O$_2$ (649.68)
Mass spectrum: (M+H)$^+$=536
Retention time (Method 1): 3.82 min Example 6

1-{3-[(R)-2-[3-(phenylsulphonylamino)-phenyl]-2-hydroxy-ethylamino]-3-methyl-butyl}-1H-indole-5-carboxylic acid-hydrotrifluoroacetate

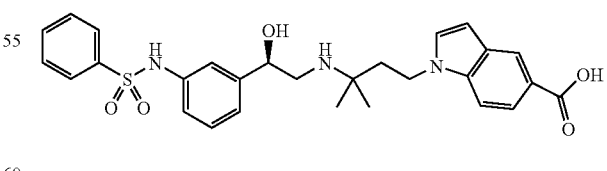

xCF$_3$COOH

Prepared analogously to Example 4 by saponification of methyl 1-{3-[(R)-2-[3-(phenylsulphonylamino)-phenyl]-2-hydroxy-ethylamino]-3-methyl-butyl}-1H-indole-5-carboxylate hydrotrifluoroacetate (Example 5) with sodium hydroxide solution (17 hours) and acidifying with TFA.

Yield: 53% of theory
$C_{28}H_{31}N_3O_5S \times C_2HF_3O_2$ (635.65)
Mass spectrum: $(M+H)^+ = 522$
retention time (Method 1): 8.67 min
Enantiomeric excess (Method 3): 97.9% ee The free base (zwitterion; 1-{3-[(R)-2-[3-(phenylsulphonylamino)-phenyl]-2-hydroxy-ethylamino]-3-methyl-butyl}-1H-indole-5-carboxylic acid) is prepared from an aqueous solution of 1-{3-[(R)-2-[3-(phenylsulphonylamino)-phenyl]-2-hydroxy-ethylamino]-3-methyl-butyl}-1H-indole-5-carboxylic acid-hydrotrifluoroacetate by adjusting the pH with sodium hydroxide solution to pH 7.6. Then the precipitate is filtered off, washed with water and dried in the vacuum dryer.

Example 7

Isopropyl 1-{3-[(R)-2-[3-(phenylsulphonylamino)-phenyl]-2-hydroxy-ethylamino]-3-methyl-butyl}-1H-indole-5-carboxylate hydrotrifluoroacetate

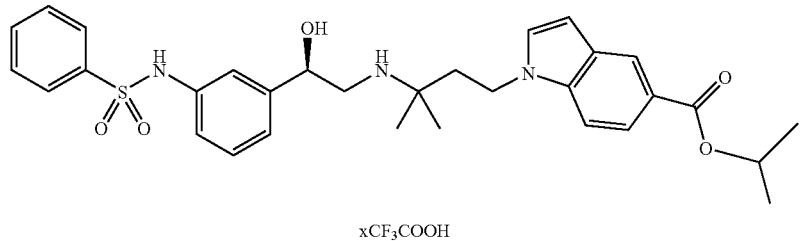

xCF₃COOH 240 mg (0.36 mmol) methyl 1-{3-[(R)-2-[3-(phenylsulphonylamino)-phenyl]-2-hydroxy-ethylamino]-3-methyl-butyl}-1H-indole-5-carboxylate (Example 5) are dissolved in 5 ml 2-propanol and combined with 19 mg (0.36 mmol) sodium methoxide. The mixture is stirred for 17 hours at ambient temperature and then acidified with TFA while cooling with ice. Then the solvent is eliminated in vacuo and the residue is chromatographed on Microsorb C18-reverse-phase [acetonitrile (0.1% TFA)/water (0.13% TFA)=10:90→100:0].

Yield: 88 mg (37% of theory)
$C_{31}H_{37}N_3O_5S \times C_2HF_3O_2$ (677.73)
Mass spectrum: $(M+H)^+ = 564$
retention time HPLC-MS: 3.42 min

Example 8

Butyl 1-{3-[(R)-2-[3-(phenylsulphonylamino)-phenyl]-2-hydroxy-ethylamino]-3-methyl-butyl}-1H-indole-5-carboxylate hydrotrifluoroacetate

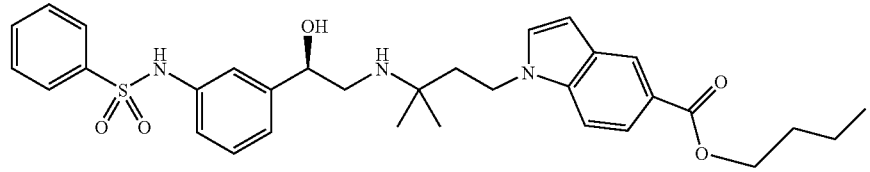

CF₃COOH

Prepared analogously to Example 7 by reacting methyl 1-{3-[(R)-2-[3-(phenylsulphonylamino)-phenyl]-2-hydroxy-ethylamino]-3-methyl-butyl}-1H-indole-5-carboxylate with sodium methoxide in n-butanol.

Yield: 31% of theory
$C_{32}H_{39}N_3O_5S \times C_2HF_3O_2$ (691.76)
Mass spectrum: $(M+H)^+ = 578$
retention time (Method 1): 3.62 min

Example 9

N-(3-{(R)-2-[3-(5-(methylsulphanyl)-indol-1-yl)-1,1-dimethyl-propylamino]-1-hydroxy-ethyl}-phenyl)-benzenesulphonamide-hydrotrifluoroacetate

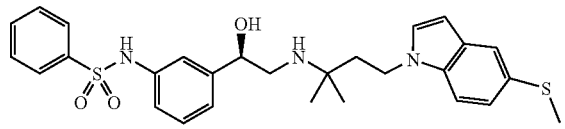

xCF₃COOH

Prepared analogously to Example 1 by reacting N—[(R)-3-oxiranyl-phenyl]-dibenzenesulphonamide (Component I) with 1-(3-amino-3-methyl-butyl)-5-(methylsulphanyl)-indole (free base from Component V), subsequent reaction with sodium hydroxide solution (1.5 hour) and acidification with TFA.

Yield: 20% of theory
$C_{28}H_{33}N_3O_3S_2 \times C_2HF_3O_2$ (637.73)
Mass spectrum: $(M+H)^+=524$
$R_f=0.37$ (silica gel; DCM/methanol/aq. $NH_3=95:5:0.1$)

Example 10

Ethyl 1-{3-[(R)-2-[3-(phenylsulphonylamino)-phenyl]-2-hydroxy-ethylamino]-3-methyl-butyl}-1H-indole-5-carboxylate hydrotrifluoroacetate

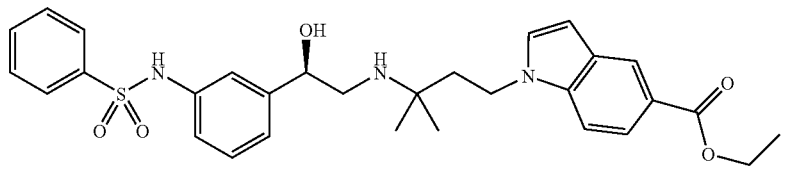

xCF₃COOH

Prepared analogously to Example 7 by reacting methyl 1-{3-[(R)-2-[3-(phenylsulphonylamino)-phenyl]-2-hydroxy-ethylamino]-3-methyl-butyl}-1H-indole-5-carboxylate with sodium hydroxide in ethanol.

Yield: 31% of theory
$C_{30}H_{35}N_3O_5S$ (549.68); $C_{30}H_{35}N_3O_5S \times C_2HF_3O_2$ (663.71)
Mass spectrum: $(M+H)^+=550$
retention time (Method 1): 3.00 min

TABLE 2

Prepared analogously to Example 1 epoxide ring opening with the corresponding aminoindole (Components VI-IX) from N-[(R)-3-oxiranyl-phenyl]-dibenzenesulphonamide (Component II) and subsequent basic benzenesulphonyl cleaving. The compounds are prepared as free bases or hydrotrifluoroacetate salts.

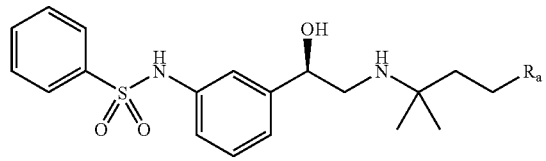

| Example | $R_a$ group | name | DC $R_f$ | MS $(M+H)^+$ | HPLC retention time (min.) | formula free base | yield | molar mass |
|---|---|---|---|---|---|---|---|---|
| 11 | | N-{3-[(R)-1-hydroxy-2-(3-indol-1-yl-1,1-dimethyl-propylamino)-ethyl]-phenyl}-benzenesulphonamide | 0.56 KG DCM/MeOH/NH₃ 9/1/0.1 | 478 | | $C_{27}H_{31}N_3O_3S$ | 16% | 477.63 |

TABLE 2-continued

Prepared analogously to Example 1 epoxide ring opening with the corresponding aminoindole (Components VI-IX) from N-[(R)-3-oxiranyl-phenyl]-dibenzenesulphonamide (Component II) and subsequent basic benzenesulphonyl cleaving. The compounds are prepared as free bases or hydrotrifluoroacetate salts.

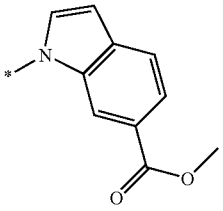

| Example | $R_a$ group | name | DC $R_f$ | MS $(M + H)^+$ | HPLC retention time (min.) | formula free base | yield | molar mass |
|---|---|---|---|---|---|---|---|---|
| 12 | 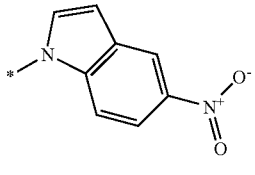 | methyl 1-{3-[(R)-2-[3-(phenylsulphonyl-amino)-phenyl]-2-hydroxy-ethylamino]-3-methyl-butyl}-1H-indole-6-carboxylate | 0.56 KG DCM/MeOH/NH$_3$ 9/1/0.1 | 536 | | $C_{29}H_{33}N_3O_5S$ | 31% | 535.67 |
| 13 | 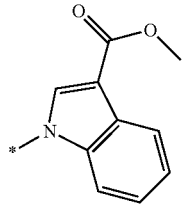 | N-(3-{(R)-2-]1,1-dimethyl-3-(5-nitro-indol-1-yl)-propylamino]-1-hydroxy-ethyl}-phenyl)-benzenesulphon-amide | 0.33 KG DCM/MeOH/NH$_3$ 95/5/0.1 | 523 | | $C_{27}H_{30}H_4O_5S$ | 45% | 522.6 |
| 14 | 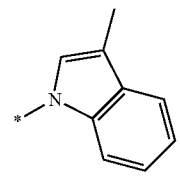 | methyl 1-{3-[(R)-2-[3-(phenylsulphonyl-amino)-phenyl]-2-hydroxy-ethylamino]-3-methyl-butyl}-1H-indole-3-carboxylate | 0.17 KG DCM/MeOH/NH$_3$ 95/5/0.1 | 536 | | $C_{29}H_{33}N_3O_5S$ | 38% | 535.67 |
| 15 | | N-(3-{(R)-2-[1,1-dimethyl-3-(3-methyl-indol-1-yl)-propylamino]-1-hydroxy-ethyl}-phenyl)-benzenesulphon-amide | 0.63 KG DCM/MeOH/NH$_3$ 90/10/0.1 | 492 | | $C_{28}H_{33}N_3O_3S$ | 39% | 491.66 |

TABLE 2-continued

Prepared analogously to Example 1 epoxide ring opening with the corresponding aminoindole (Components VI-IX) from N-[(R)-3-oxiranyl-phenyl]-dibenzenesulphonamide (Component II) and subsequent basic benzenesulphonyl cleaving. The compounds are prepared as free bases or hydrotrifluoroacetate salts.

| Example | $R_a$ group | name | DC $R_f$ | MS $(M + H)^+$ | HPLC retention time (min.) | formula free base | yield | molar mass |
|---|---|---|---|---|---|---|---|---|
| 16 | | methyl (1-{3-[(R)-2-[3-(phenylsulphonyl-amino)-phenyl]-2-hydroxy-ethylamino]-3-methyl-butyl}-1H-indol-3-yl)-acetate | 0.55 KG DCM/MeOH NH$_3$ 90/10/0.1 | 550 | | $C_{50}H_{35}N_3O_5S$ | 25% | 549.69 |
| 17 | | N-[3-((R)-2-{1,1-dimethyl-3-[5-(2,2 2-trifluoro-acetyl)-indol-1-yl]-propylamino}-1-hydroxy-ethyl)-phenyl]-benzenesulphon-amide | 0.42 KG DCM/MeOH/NH$_3$ 9/1/0.1 | 574 | | $C_{28}H_{30}F_3N_3O_4S$ | 29% | 573.64 |

Example 18

N-[3-(2-{1,1-dimethyl-3-[5-(5-oxo-2,5-dihydro-[1,2,4]oxadiazol-3-yl)-indol-1-yl]-propylamino}-1-hydroxy-ethyl)-phenyl]-benzenesulphonamide-hydrotrifluoroacetate

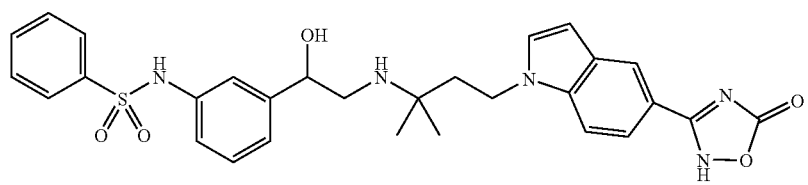

xCF$_3$COOH

Prepared analogously to Example 3 by reductive amination of N-[3-(2-ethoxy-2-hydroxyacetyl)-phenyl]-benzenesulphonamide (Component I) and 3-[1-(3-amino-3-methyl-butyl)-1H-indol-5-yl]-2H-[1,2,4]oxadiazol-5-one-hydrotrifluoroacetate (Component IX). The product is chromatographed on Microsorb C18-reverse-phase [acetonitrile (0.1% TFA)/water (0.13% TFA)=10:90→100:0].

Yield: 59% of theory $C_{29}H_{31}N_5O_5S \times CF_3CO_2H$ (675.68)

Mass spectrum: $(M+H)^+=562$ $R_f=0.27$ (silica gel; DCM/methanol/NH$_4$OH=90:10:0.1)

Example 19

N-[3-((R)-1-hydroxy-2-{3-[5-(2-methanesulphonyl-acetyl)-indol-1-yl]-1,1-dimethyl-propylamino}-ethyl)-phenyl]-benzenesulphonamide-hydrotrifluoroacetate

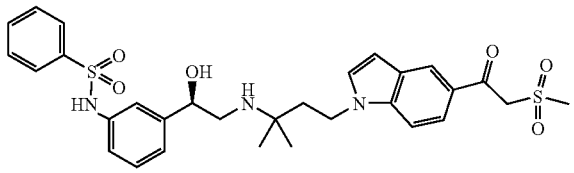

Prepared analogously to Example 1 by reacting N—[(R)-3-oxiranyl-phenyl]-dibenzenesulphonamide (Component I) with 1-[1-(3-amino-3-methyl-butyl)-1H-indol-5-yl]-2-methanesulphonyl-ethanone (Component X), subsequent reaction with 4N sodium hydroxide solution (two hours at RT). After acidifying with TFA the product is chromatographed on Microsorb C18-reverse-phase [acetonitrile (0.1% TFA)/water (0.13% TFA)=10:90→100:0].

Yield: (99% of theory)
$C_{30}H_{35}N_3O_6S_2 \times C_2HF_3O_2$ (711.77)
Mass spectrum: $(M+H)^+=598$
Retention time (Method 1): 2.59 min

Example 20

N-(3-{(R)-2-[3-(5-amino-indol-1-yl)-1,1-dimethyl-propylamino]-1-hydroxy-ethyl}-phenyl)-benzenesulphonamide-hydrotrifluoroacetate

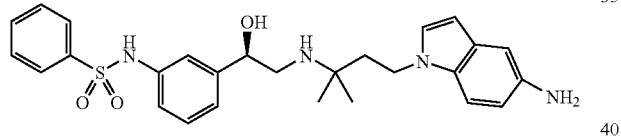

Raney-Ni (40 mg) is added to a solution of N-(3-{(R)-2-[1,1-dimethyl-3-(5-nitro-indol-1-yl)-propylamino]-1-hydroxy-ethyl}-phenyl)-benzenesulphonamide (Example 13; 200 mg, 0.31 mmol) in 5 ml of ethyl acetate and 5 ml of methanol. The reaction mixture is stirred for 7 hours at RT under 3 bar hydrogen. The Raney-Ni is filtered off, and the filtrate is freed from the solvent in vacuo. The residue is chromatographed on Microsorb C18-reverse-phase [acetonitrile (0.1% TFA)/water (0.13% TFA)=10:90→100:0].

Yield: 155 mg (68% of theory)

$C_{27}H_{32}N_4O_3S \times 2C_2HF_3O_2$ (726.81)

Mass spectrum: $(M+H)^+=493$ $R_f=0.33$ (silica gel; DCM/methanol/ammonia=90:10:0.1)

The free base (N-(3-{(R)-2-[3-(5-amino-indol-1-yl)-1,1-dimethyl-propylamino]-1-hydroxy-ethyl}-phenyl)-benzenesulphonamide) is prepared as follows: A mixture of N-(3-{(R)-2-[3-(5-amino-indol-1-yl)-1,1-dimethyl-propylamino]-1-hydroxy-ethyl}-phenyl)-benzenesulphonamide-hydrotrifluoroacetate) in chloroform and saturated sodium carbonate solution is stirred for 10 minutes. The organic phase is separated off, dried on sodium sulphate and the solvent is eliminated in vacuo.

Example 21

21.A: N-(3-{(R)-2-[1,1-dimethyl-3-(5-ureido-indol-1-yl)-propylamino]-1-hydroxy-ethyl}-phenyl)-benzenesulphonamide-hydrotrifluoroacetate

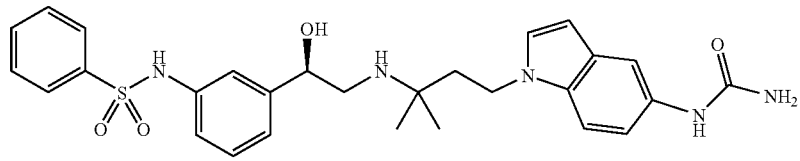

21.B: N-(1-{3-[(R)-2-[3-(phenylsulphonylamino)-phenyl]-2-hydroxy-ethylamino]-3-methyl-butyl}-1H-indol-5-yl)-acetamide-hydrotrifluoroacetate

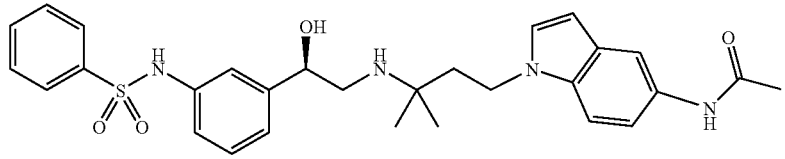

The free base of N-(3-{(R)-2-[3-(5-amino-indol-1-yl)-1,1-dimethyl-propylamino]-1-hydroxy-ethyl}-phenyl)-benzenesulphonamide-hydrotrifluoroacetate (free base from Example 20; 100 mg, 0.20 mmol) is dissolved in 3.5 ml acetic acid and 3.5 ml of water. Then potassium cyanate (36.2 mg, 0.45 mmol) is added. The reaction mixture is stirred for 3 hours at RT, the solvent is eliminated in vacuo and chromatographed on Microsorb C18-reverse-phase [acetonitrile (0.1% TFA)/water (0.13% TFA)=10:90→100:0]. Two compounds are isolated.

21.A: N-(3-{(R)-2-[1,1-dimethyl-3-(5-ureido-indol-1-yl)-propylamino]-1-hydroxy-ethyl}-phenyl)-benzenesulphonamide-hydrotrifluoroacetate Yield: 60 mg (45% of theory)
$C_{28}H_{33}N_5O_4S \times C_2HF_3O_2$ (649.68)
Mass spectrum: $(M+H)^+=536$
$R_f=0.34$ (silica gel; DCM/methanol/ammonia=90:10:0.1)

21.B: N-(1-{3-[(R)-2-[3-(phenylsulphonylamino)-phenyl]-2-hydroxy-ethylamino]-3-methyl-butyl}-1H-indol-5-yl)-acetamide-hydrotrifluoroacetate Yield: 30 mg (23% of theory)
$C_{29}H_{34}N_4O_4S \times C_2HF_3O_2$ (648.69)
Mass spectrum: $(M+H)^+=535$
$R_f=0.40$ (silica gel; DCM/methanol/ammonia=90:10:0.1)

Example 22

N-[3-((R)-2-{3-[5-(3-hexyl-ureido)-indol-1-yl]-1,1-dimethyl-propylamino}-1-hydroxy-ethyl)-phenyl]-benzenesulphonamide-hydrotrifluoroacetate

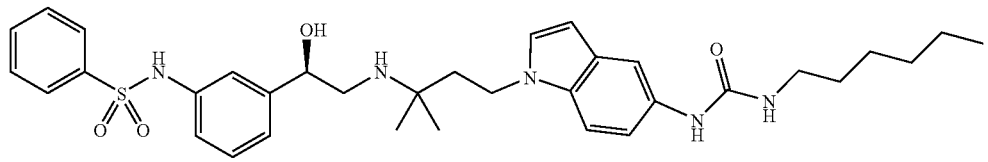

The free base of N-(3-{(R)-2-[3-(5-amino-indol-1-yl)-1,1-dimethyl-propylamino]-1-hydroxy-ethyl}-phenyl)-benzenesulphonamide-hydrotrifluoroacetate (free base from Example 20; 100 mg, 0.20 mmol) is dissolved in 3 ml THF and combined with hexylisocyanate (32.3 μl, 0.22 mmol). The reaction mixture is stirred for 18 hours at RT, the solvent is eliminated in vacuo and the residue is chromatographed on Microsorb C18-reverse-phase [acetonitrile (0.1% TFA)/water (0.13% TFA)=10:90→100:0].
Yield: 50 mg (34% of theory)
$C_{34}H_{45}N_5O_4S \times C_2HF_3O_2$ (733.84)
Mass spectrum: $(M+H)^+=620$
$R_f=0.18$ (silica gel; DCM/methanol/ammonia=95:5:0.1)

Example 23

N-[3-((R)-2-{1,1-dimethyl-3-[5-(3-phenyl-ureido)-indol-1-yl]-propylamino}-1-hydroxy-ethyl)-phenyl]-benzenesulphonamide-hydrotrifluoroacetate

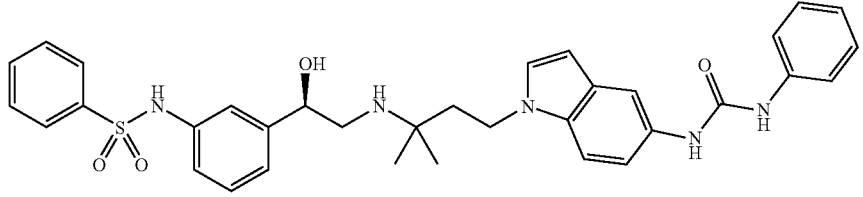

The free base of N-(3-{(R)-2-[3-(5-amino-indol-1-yl)-1,1-dimethyl-propylamino]-1-hydroxy-ethyl}-phenyl)-benzenesulphonamide-hydrotrifluoroacetate (free base from Example 20; 100 mg, 0.20 mmol) is dissolved in 3 ml THF and then combined with phenylisocyanate (24 μl, 0.22 mmol). The reaction mixture is stirred for 5 hours at RT, the solvent is eliminated in vacuo and chromatographed on Microsorb C18-reverse-phase [acetonitrile (0.1% TFA)/water (0.13% TFA)=10:90→100:0].
Yield: 30 mg (20% of theory)
$C_{34}H_{37}N_5O_4S \times C_2HF_3O_2$ (725.78)
Mass spectrum: $(M+H)^+=612$
$R_f=0.15$ (silica gel; DCM/methanol/ammonia=95:5:0.1)

Example 24

N-(3-{(R)-1-hydroxy-2-[3-(5-methanesulphony-lamino-indol-1-yl)-1,1-dimethyl-propylamino]-ethyl}-phenyl)-benzenesulphonamide-hydrotrifluoroacetate

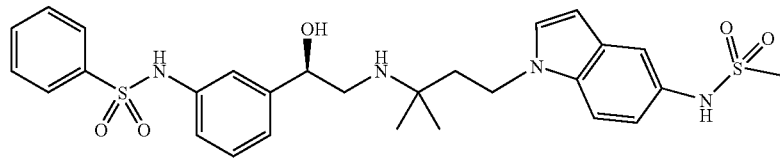

The free base of N-(3-{(R)-2-[3-(5-amino-indol-1-yl)-1,1-dimethyl-propylamino]-1-hydroxy-ethyl}-phenyl)-benzenesulphonamide-hydrotrifluoroacetate (free base from Example 20; 100 mg, 0.20 mmol) is dissolved in 5 ml DCM. Then pyridine (20 µl, 0.24 mmol) is added. The reaction mixture is cooled to 0° C. Methanesulphonic acid chloride (16 µl, 0.20 mmol) is added. After 18 hours stirring at RT the solvent is eliminated in vacuo and the residue is chromatographed on Microsorb C18-reverse-phase [acetonitrile (0.1% TFA)/water (0.13% TFA)=10:90→100:0].

Yield: 65 mg (56% of theory)
$C_{28}H_{34}N_4O_5S_2 \times C_2HF_3O_2$ (684.75)
Mass spectrum: $(M+H)^+=571$
$R_f=0.20$ (silica gel; DCM/methanol/ammonia=95:5:0.1)

Example 25

N-(1-{3-[(R)-2-[3-(phenylsulphonylamino)-phenyl]-2-hydroxy-ethylamino]-3-methyl-butyl}-1H-indol-5-yl)-hexanoic acid-amide-hydrotrifluoroacetate

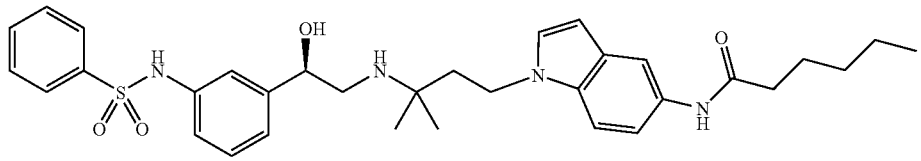

The free base of N-(3-{(R)-2-[3-(5-amino-indol-1-yl)-1,1-dimethyl-propylamino]-1-hydroxy-ethyl}-phenyl)-benzenesulphonamide-hydrotrifluoroacetate (free base from Example 20; 100 mg, 0.20 mmol), hexanecarboxylic acid (24 mg, 0.24 mmol) and DIPEA (69 µl, 0.41 mmol) are dissolved in 3 ml THF. Then HOBt (27.4 mg, 0.20 mmol) and TBTU (71.7 mg, 0.22 mmol) are added. The reaction mixture is stirred for 2 hours at RT, the solvent is eliminated in vacuo and the residue is chromatographed on Microsorb C18-reverse-phase [acetonitrile (0.1% TFA)/water (0.13% TFA)=10:90→100:0].

Yield: 100 mg (70% of theory)
$C_{33}H_{42}N_4O_4S \times C_2HF_3O_2$ (704.80)
Mass spectrum: $(M+H)^+=591$
$R_f=0.20$ (silica gel; DCM/methanol/ammonia=95:5:0.1)

Example 26

N-(1-{3-[(R)-2-[3-(phenylsulphonylamino)-phenyl]-2-hydroxy-ethylamino]-3-methyl-butyl}-1H-indol-5-yl)-cyclopropanecarboxylic acid-amide-hydrotrifluoroacetate

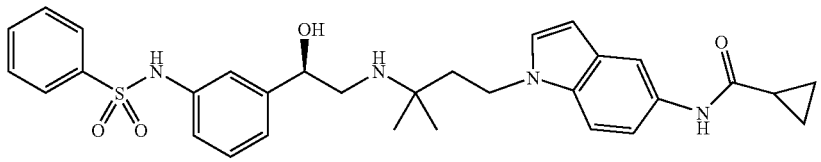

Prepared analogously to Example 25 by amide linking with cyclopropanecarboxylic acid.

Yield: 95 mg (69% of theory)
$C_{31}H_{36}N_4O_4S \times C_2HF_3O_2$ (674.73)
Mass spectrum: $(M+H)^+=561$
$R_f=0.20$ (silica gel; DCM/methanol/ammonia=95:5:0.1)

Example 27

N-(1-{3-[(R)-2-[3-(phenylsulphonylamino)-phenyl]-2-hydroxy-ethylamino]-3-methyl-butyl}-1H-indol-5-yl)-2-benzyloxy-acetamide hydrotrifluoroacetate

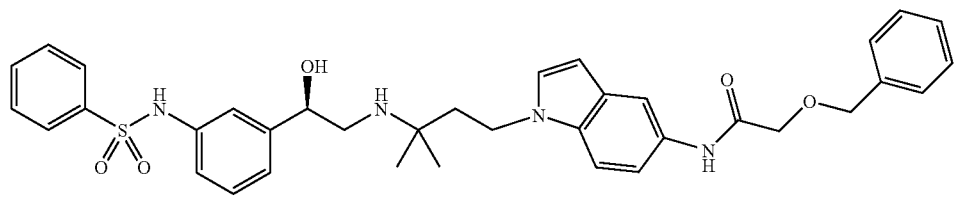

Prepared analogously to Example 25 by amide linking with benzyloxyacetic acid.
Yield: 65 mg (42% of theory)
$C_{36}H_{40}N_4O_5S \times C_2HF_3O_2$ (754.82)
Mass spectrum: $(M+H)^+=641$
$R_f=0.12$ (silica gel; DCM/methanol/ammonia=95:5:0.1)

Example 28

N-(1-{3-[(R)-2-[3-(phenylsulphonylamino)-phenyl]-2-hydroxy-ethylamino]-3-methyl-butyl}-1H-indol-5-yl)-2-cyano-acetamide-hydrotrifluoroacetate

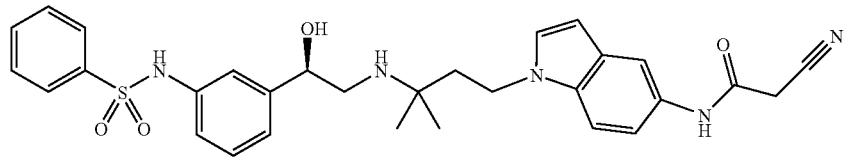

Prepared analogously to Example 25 by amide linking with cyanoacetic acid.
Yield: 50 mg (37% of theory)
$C_{30}H_{33}N_5O_4S \times C_2HF_3O_2$ (673.70)
Mass spectrum: $(M+H)^+=560$
$R_f=0.11$ (silica gel; DCM/methanol/ammonia=95:5:0.1)

Example 29

N-(1-{3-[(R)-2-[3-(phenylsulphonylamino)-phenyl]-2-hydroxy-ethylamino]-3-methyl-butyl}-1H-indol-5-yl)-(2S,3S)-2-amino-3-methyl-pentanoic acid-amide-hydroformate

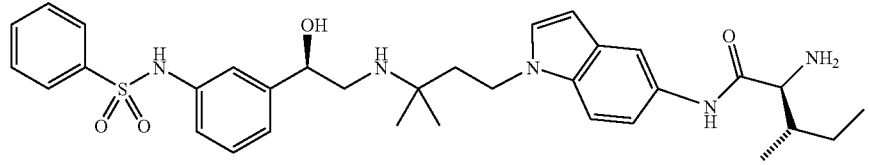

a. benzyl [(1S,2S)-1-(1-{3-[(R)-2-[3-(phenylsulpho-nylamino)-phenyl]-2-hydroxy-ethylamino]-3-methyl-butyl}-1H-indol-5-ylcarbamoyl)-2-methyl-butyl]-carbamate-hydroformate The free base of N-(3-{(R)-2-[3-(5-amino-indol-1-yl)-1,1-dimethyl-propylamino]-1-hydroxy-ethyl}-phenyl)-benzene-sulphonamide-hydrotrifluoroacetate (free base from Example 20; 100 mg, 0.20 mmol), N-(benzyloxycarbonyl)-L-isoleucine (Cbz-L-isoleucin) (53 mg, 0.20 mmol) and DIPEA (69 µl, 0.41 mmol) are dissolved in 3 ml THF. Then HOBt (27.4 mg, 0.20 mmol) and TBTU (71.7 mg, 0.22 mmol) are added. The reaction mixture is stirred for 2 hours at RT. Then the solvent is eliminated in vacuo and the residue is chromatographed on Chromolith C18-reverse-phase [acetonitrile (0.1% formic acid)/water (0.1% formic acid)=10:90→90:10].

Yield: 106 mg (71% of theory)
$C_{41}H_{49}N_5O_6S \times HCO_2H$ (785.95)
Mass spectrum: $(M+H)^+=740$
$R_f=0.53$ (silica gel; DCM/methanol/ammonia=90:10:0.1)

b. N-(1-{3-[(R)-2-[3-(phenylsulphonylamino)-phenyl]-2-hydroxy-ethylamino]-3-methyl-butyl}-1H-indol-5-yl)-(2S,3S)-2-amino-3-methyl-pentanoic acid-amide-hydroformate 10% palladium on charcoal (20 mg) are added to a solution of benzyl [(1S,2S)-1-(1-{3-[(R)-2-[3-(phenylsulphonylamino)-phenyl]-2-hydroxy-ethylamino]-3-methyl-butyl}-1H-indol-5-ylcarbamoyl)-2-methyl-butyl]-carbamate-hydroformate (106 mg, 0.14 mmol) in 7 ml of methanol. The reaction mixture is stirred for 2 hours at RT under 3 bar hydrogen atmosphere. Then the catalyst is removed by suction filtering and the filtrate is freed from the solvent in vacuo.

Yield: 60 mg (64% of theory)
$C_{33}H_{43}N_5O_4S \times HCO_2H$ (651.82)
Mass spectrum: $(M+H)^+=606$
$R_f=0.49$ (silica gel; DCM/methanol/ammonia=90:10:0.1)

Example 30

N-(1-{3-[(R)-2-[3-(phenylsulphonylamino)-phenyl]-2-hydroxy-ethylamino]-3-methyl-butyl}-1H-indol-5-yl)-(2S)-2-amino-3-methyl-butyric acid-amide-hydroformate

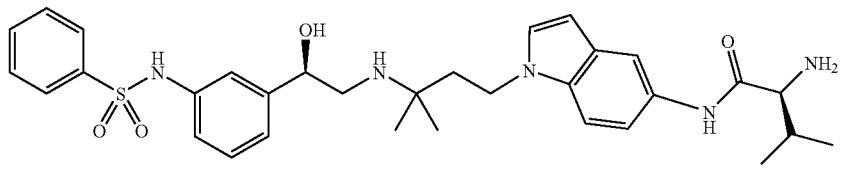

Prepared analogously to Example 29 by amide linking with N-(benzyloxycarbonyl)-L-valine (Cbz-L-valine).
Yield: 62 mg (76% of theory)
$C_{32}H_{41}N_5O_4S \times HCO_2H$ (637.79)
Mass spectrum: $(M+H)^+=592$
$R_f=0.47$ (silica gel; DCM/methanol/ammonia=90:10:0.1)

Example 31

N-(1-{3-[(R)-2-[3-(phenylsulphonylamino)-phenyl]-2-hydroxy-ethylamino]-3-methyl-butyl}-1H-indol-5-yl)-(2S)-2-amino-propionic acid-amide-hydroformate

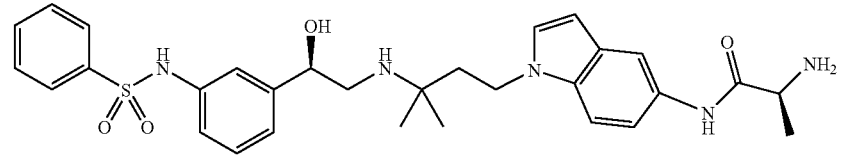

Prepared analogously to Example 29 by amide linking with N-(benzyloxycarbonyl)-L-alanine (Cbz-L-alanine).
Yield: 78 mg (89% of theory)
$C_{30}H_{37}N_5O_4S \times HCO_2H$ (609.72)
Mass spectrum: $(M+H)^+=564$
$R_f=0.27$ (silica gel; DCM/methanol/ammonia=90:10:0.1)

Example 32

1-{3-[(R)-2-[3-(phenylsulphonylamino)-phenyl]-2-hydroxy-ethylamino]-3-methyl-butyl}-1H-indole-5-carboxylic acid-amide-hydrotrifluoroacetate

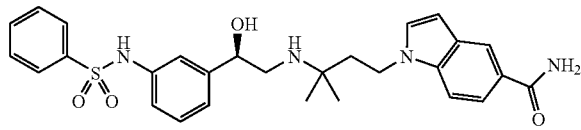

EDCI (75 mg, 0.39 mmol) and HOBt (49 mg, 0.36 mmol) are added to a solution of 1-{3-[(R)-2-[3-(phenylsulphonylamino)-phenyl]-2-hydroxy-ethylamino]-3-methyl-butyl}-1H-indole-5-carboxylic acid-hydrotrifluoroacetate (Example 6; 100 mg, 0.16 mmol) in 2 ml DMF. Then the reaction mixture is stirred for 40 minutes at RT and DIPEA (51 mg, 0.39 mmol) is added. After 10 minutes stirring at RT a solution of ammonia in dioxane (0.5M; 10 ml, 5.0 mmol) is added. After 20 hours stirring at RT the solvent is eliminated in vacuo and the residue is chromatographed on Microsorb C18-reverse-phase [acetonitrile (0.1% TFA)/water (0.13% TFA)=10:90→100:0].

Yield: 71 mg (72% of theory)
$C_{28}H_{32}N_4O_4S \times C_2HF_3O_2$ (634.67)
Mass spectrum: $(M+H)^+=521$
retention time (Method 1): 2.30 min

Example 33

1-{3-[(R)-2-[3-(phenylsulphonylamino)-phenyl]-2-hydroxy-ethylamino]-3-methyl-butyl}-1H-indole-5-carboxylic acid-methylamide-hydrotrifluoroacetate

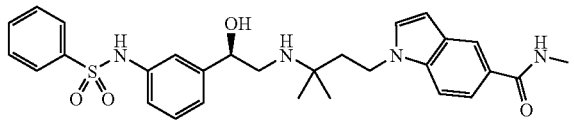

EDCI (75 mg, 0.39 mmol) and HOBt (49 mg, 0.36 mmol) are added to a solution of 1-{3-[(R)-2-[3-(phenylsulphonylamino)-phenyl]-2-hydroxy-ethylamino]-3-methyl-butyl}-1H-indole-5-carboxylic acid-hydrotrifluoroacetate (Example 6; 100 mg, 0.16 mmol) in 2 ml DMF. Then the reaction mixture is stirred for 60 minutes at RT and combined with DIPEA (66 µl, 0.39 mmol). After 10 minutes stirring at RT a solution of methylamine in THF (2.0M; 2.5 ml, 5.0 mmol) is added. After 48 hours stirring at RT the solvent is eliminated in vacuo and the residue is chromatographed on Microsorb C18-reverse-phase [acetonitrile (0.1% TFA)/water (0.13% TFA)=10:90→100:0].

Yield: 65 mg (64% of theory)
$C_{29}H_{34}N_4O_4S \times C_2HF_3O_2$ (648.69)
Mass spectrum: $(M+H)^+=535$
retention time (Method 1): 2.39 min

Example 34

1-{3-[(R)-2-[3-(phenylsulphonylamino)-phenyl]-2-hydroxy-ethylamino]-3-methyl-butyl}-1H-indole-5-carboxylic acid-dimethylamide

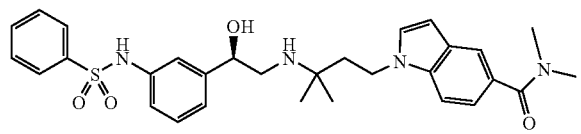

EDCI (75 mg, 0.39 mmol) and HOBt (49 mg, 0.36 mmol) are added to a solution of 1-{3-[(R)-2-[3-(phenylsulphonylamino)-phenyl]-2-hydroxy-ethylamino]-3-methyl-butyl}-1H-indole-5-carboxylic acid-hydrotrifluoroacetate (Example 6; 100 mg, 0.16 mmol) in 2 ml DMF. Then the reaction mixture is stirred for 60 minutes at RT and combined with DIPEA (66 µl, 0.39 mmol). After 10 minutes stirring at RT a solution of dimethylamine in THF (2.0M; 2.5 ml, 5.0 mmol) is added. After 22 hours stirring at RT the solvent is eliminated in vacuo and the residue is chromatographed on Microsorb C18-reverse-phase [acetonitrile (0.1% TFA)/water (0.13% TFA)=10:90→100:0]. After freeze-drying the salt is converted into the base in ethyl acetate with semisaturated sodium hydrogen carbonate solution.

Yield: 58 mg (67% of theory)
$C_{30}H_{36}N_4O_4S$ (548.70)
Mass spectrum: $(M+H)^+=549$
retention time (Method 1): 2.51 min

Example 35

1-{3-[(R)-2-[3-(phenylsulphonylamino)-phenyl]-2-hydroxy-ethylamino]-3-methyl-butyl}-N-cyano-1H-indole-5-carboxylic acid-amide-hydrotrifluoroacetate

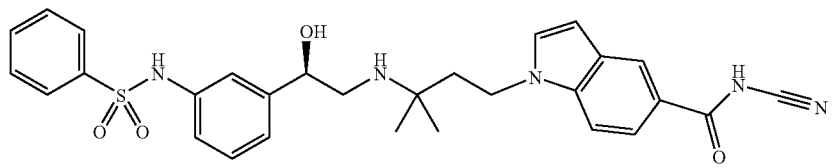

EDCI (75 mg, 0.39 mmol) and HOBt (49 mg, 0.36 mmol) are added to a solution of 1-{3-[(R)-2-[3-(phenylsulphonylamino)-phenyl]-2-hydroxy-ethylamino]-3-methyl-butyl}-1H-indole-5-carboxylic acid-hydrotrifluoroacetate (Example 6; 100 mg, 0.16 mmol) in 2 ml DMF. Then the reaction mixture is stirred for 60 minutes at RT and then combined with DIPEA (66 μl, 0.39 mmol). After 10 minutes stirring at RT cyanamide (210 mg, 5.0 mmol) is added. After 22 hours stirring at RT the solvent is eliminated in vacuo and the residue is chromatographed on Microsorb C18-reverse-phase [acetonitrile (0.1% TFA)/water (0.13% TFA)=10:90→100:0].

Yield: 52 mg (50% of theory)
$C_{29}H_{31}N_5O_4S \times C_2HF_3O_2$ (659.68)
Mass spectrum: $(M+H)^+=546$
retention time (Method 1): 2.56 min

TABLE 3

Prepared analogously to Example 35 by amide linking with the corresponding substituted amine (see $R_b$ group in Table 3).

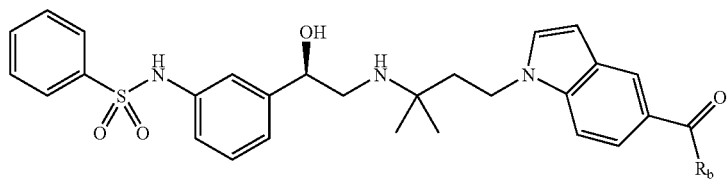

| Example | $R_b$ group | name | DC $R_f$ | MS $(M + H)^+$ | HPLC retention time (min.) | yield | formula free base | molar mass |
|---|---|---|---|---|---|---|---|---|
| 36 | | 1-{3-[(R)-2-[3-(phenylsulphonylamino)-phenyl]-2-hydroxy-ethylamino]-3-methyl-butyl}-1H-indole-5-hydroxamic acid | | 537 | 2.22 meth. 1 | 59% | $C_{28}H_{32}N_4O_5S$ | |
| 37 | | 1-{3-[(R)-2-[3-(phenylsulphonyl-amino)-phenyl]-2-hydroxy-ethylamino]-3-methyl-butyl}-1H-indole-5-carboxylic acid-methoxy-amide | | 551 | 2.37 meth. 1 | 57% | $C_{29}H_{34}N_4O_5S$ | 550.68 |
| 38 | | N-(3-{(R)-2-[3-(5-hydrazinocarbonyl-indol-1-yl)-1,1-dimethyl-propylamino]-1-hydroxy-ethyl}-phenyl)-benzenesulphonamide | | 536 | 2.10 meth. 1 | 48% | $C_{28}H_{33}N_5O_4S$ | 535.67 |
| 39 | | methyl (S)-2-[(1-{3-[(R)-2-[3-(phenylsulphonyl-amino)-phenyl]-2-hydroxy-ethylamino]-3-methyl-butyl}-1H-indol-5-ylcarbonyl)-amino]-propionate | | 607 | 2.56 meth. 1 | 73% | $C_{32}H_{38}N_4O_6S$ | 606.74 |
| 40 | | methyl (S)-2-[(1-{3-[(R)-2-[3-(phenylsulphonyl-amino)-phenyl]-2-hydroxy-ethylamino]-3-methyl-butyl}-1H-indol-5-ylcarbonyl)-amino]-3-methyl-butyrate | | 635 | 2.91 meth. 1 | 98% | $C_{34}H_{42}N_4O_6S$ | 634.79 |
| 41 | | methyl (2S,3S)-2-[(1-{3-[(R)-2-[3-(phenylsulphonyl-amino)-phenyl]-2-hydroxy-ethylamino]-3-methyl-butyl}-1H-indol-5-ylcarbonyl)-amino]-3-methyl-valerate | | 649 | 3.05 meth. 1 | 90% | $C_{35}H_{44}N_4O_6S$ | 648.81 |

TABLE 3-continued

Prepared analogously to Example 35 by amide linking with the corresponding substituted amine (see $R_b$ group in Table 3).

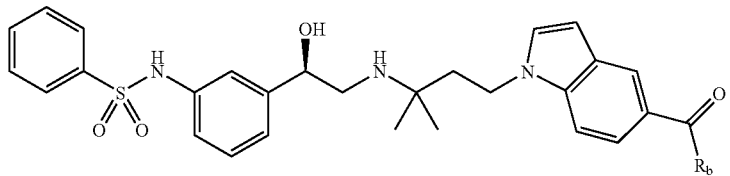

| Example | $R_b$ group | name | DC $R_f$ | MS $(M + H)^+$ | HPLC retention time (min.) | yield | formula free base | molar mass |
|---|---|---|---|---|---|---|---|---|
| 42 | | 1-{3-[(R)-2-[3-(phenylsulphonyl-amino)-phenyl]-2-hydroxy-ethylamino]-3-methyl-butyl}-1H-indole-5-carboxylic acid-butylamide | | 577 | 2.86 meth. 1 | 60% | $C_{32}H_{40}N_4O_4S$ | 576.76 |
| 43 | | 1-{3-[(R)-2-[3-(phenylsulphonyl-amino)-phenyl]-2-hydroxy-ethylamino]-3-methyl-butyl}-1H-indole-5-carboxylic acid-cyclopropylamide | | 561 | 2.55 meth. 1 | 75% | $C_{31}H_{36}N_4O_4S$ | 560.72 |
| 44 | | methyl 3-[(1-{3-[(R)-2-[3-(phenylsulphonyl-amino)-phenyl]-2-hydroxy-ethylamino]-3-methyl-butyl}-1H-indol-5-ylcarbonyl)-amino]-propionate | | 607 | 2.48 meth. 1 | 41% | $C_{32}H_{38}N_4O_6S$ | 606.74 |
| 45 | | methyl [(1-{3-[(R)-2-[3-(phenylsulphonyl-amino)-phenyl]-2-hydroxy-ethylamino]-3-methyl-butyl}-1H-indol-5-ylcarbonyl)-amino]-acetate | | 593 | 2.32 meth. 1 | 50% | $C_{31}H_{36}N_4O_6S$ | 592.71 |
| 46 | | 1-{3-[(R)-2-[3-(phenylsulphonyl-amino)-phenyl]-2-hydroxy-ethylamino]-3-methyl-butyl}-1H-indole-5-carboxylic acid-(2,2 2-trifluoro-ethyl)-amide | | 603 | 2.77 meth. 1 | 27% | $C_{30}H_{33}F_3N_4O_4S$ | 602.67 |
| 47 | | 1-{3-[(R)-2-[3-(phenylsulphonyl-amino)-phenyl]-2-hydroxy-ethylamino]-3-methyl-butyl}-1H-indole-5-carboxylic acid-(2-fluoro-ethyl)-amide | | 567 | 2.50 meth. 1 | 26% | $C_{30}H_{35}FN_4O_4S$ | 566.69 |
| 48 | | N-[3-((R)-2-{1,1-dimethyl-3-[5-(morpholin-4-ylcarbonyl)-indol-1-yl]-propylamino}-1-hydroxy-ethyl)-phenyl]-benzenesulphonamide | | 591 | 2.47 meth. 1 | 18% | $C_{32}H_{38}N_4O_5S$ | 590.74 |

TABLE 3-continued

Prepared analogously to Example 35 by amide linking with the corresponding substituted amine (see $R_b$ group in Table 3).

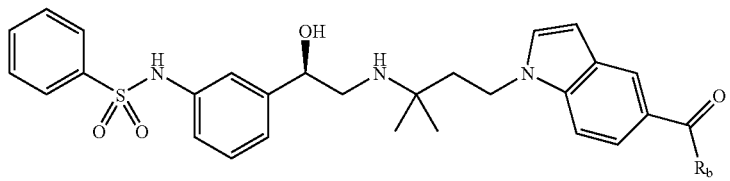

| Example | $R_b$ group | name | DC $R_f$ | MS $(M + H)^+$ | HPLC retention time (min.) | yield | formula free base | molar mass |
|---|---|---|---|---|---|---|---|---|
| 49 | *-NH-CH2-cyclopropyl | 1-{3-[(R)-2-[3-(phenylsulphonyl-amino)-phenyl]-2-hydroxy-ethylamino]-3-methyl-butyl}-1H-indole-5-carboxylic acid-cyclopropylmethyl-amide | | 575 | 2.70 meth. 1 | 20% | $C_{32}H_{38}N_4O_4S$ | 574.74 |
| 50 | *-pyrrolidinyl | N-[3-((R)-2-{1,1-dimethyl-3-[5-(pyrrolidin-1-ylcarbonyl)-indol-1-yl]-propylamino}-1-hydroxy-ethyl)-phenyl]-benzenesulphonamide | | 575 | 2.63 meth. 1 | 20% | $C_{32}H_{38}N_4O_4S$ | 574.74 |
| 51 | *-thiomorpholine-1,1-dioxide | N-[3-((R)-2-{3-[5-(1,1-dioxo-1-thiomorpholin-4-ylcarbonyl)-indol-1-yl]-1,1-dimethyl-propylamino}-1-hydroxy-ethyl)-phenyl]-benzenesulphonamide | | 639 | 3.88 meth. 1 | 24% | $C_{32}H_{38}N_4O_6S$ | 638.81 |
| 52 | *-NH-CH2CH2-SO2-CH3 | 1-{3-[(R)-2-[3-(phenylsulphonyl-amino)-phenyl]-2-hydroxy-ethylamino]-3-methyl-butyl}-1H-indole-5-carboxylic acid-(2-methane-sulphonyl-ethyl)-amide | 0.35 KG DCM/ MeOH/ NH3 90/9/1 | 627 | | 70% | $C_{31}H_{38}N_4O_6S_2$ | 626.80 |
| 53 | *-N(CH3)-N(CH3)2 | N-[3-((R)-2-{3-[5-(N',N'-dimethyl-hydrazinocarbonyl)-indol-1-yl]-1,1-dimethyl-propylamino}-1-hydroxy-ethyl)-phenyl]-benzenesulphonamide | | 564 | 2.19 meth. 1 | 36% | $C_{30}H_{37}N_5O_4S$ | 563.72 |
| 54 | *-N(CH3)-NH2 | N-[3-((R)-2-{1,1-dimethyl-3-[5-(N-methyl-hydrazinocarbonyl)-indol-1-yl]-propylamino}-1-hydroxy-ethyl)-phenyl]-benzenesulphonamide | | 550 | 2.29 meth. 1 | 69% | $C_{29}H_{35}N_5O_4S$ | 549.69 |

Example 55

(5-methyl-2-oxo-[1,3]dioxol-4-ylmethyl) 1-{3-[(R)-2-[3-(phenylsulphonylamino)-phenyl]-2-hydroxy-ethylamino]-3-methyl-butyl}-1H-indole-5-carboxylate hydrotrifluoroacetate

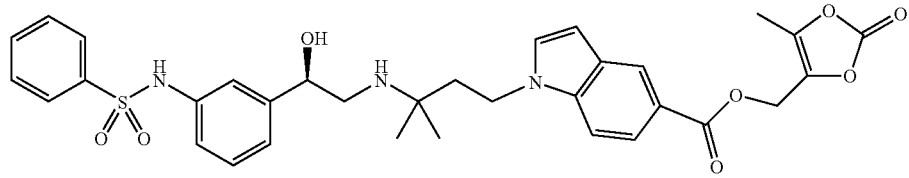

Potassium hydrogen carbonate (331 mg, 3.30 mmol) and 4-bromomethyl-5-methyl-[1,3]dioxol-2-one (Chem. Pharm. Bull. 1984, vol. 32 (6), page 2241-2248) (505 mg, 2.36 mmol) are added to a solution of 1-{3-[(R)-2-[3-(phenylsulphonylamino)-phenyl]-2-hydroxy-ethylamino]-3-methyl-butyl}-1H-indole-5-carboxylic acid-hydrotrifluoroacetate (Example 6; 1.0 g, 1.57 mmol) in 10 ml DMF. Then the reaction mixture is stirred for 18 hours at RT. Then the solid is filtered off and the filtrate is freed from the solvent in vacuo. The residue is chromatographed on silica gel (DCM/methanol/ammonia=100:0:0→90:10:0.1).

Yield: 160 mg (16% of theory)

$C_{33}H_{35}N_3O_8S$ (633.71)

Mass spectrum: $(M+H)^+=634$ $R_f=0.46$ (silica gel; DCM/methanol/ammonia=90:10:0.1)

Example 56

[2-(morpholin-4-yl)-ethyl]-{3-[(R)-2-[3-(phenylsulphonylamino)-phenyl]-2-hydroxy-ethylamino]-3-methyl-butyl}-1H-indole-5-carboxylate hydrotrifluoroacetate

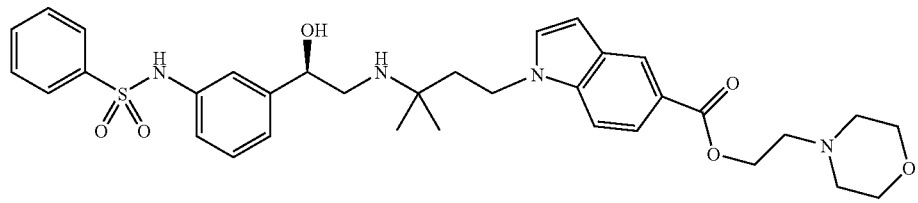

Potassium hydrogen carbonate (0.92 g, 9.2 mmol) is added to a solution of 1-{3-[(R)-2-[3-(phenylsulphonylamino)-phenyl]-2-hydroxy-ethylamino]-3-methyl-butyl}-1H-indole-5-carboxylic acid [free base (zwitterion) of Example 6; 1.2 g, 2.3 mmol] in 8 ml DMF. Then the reaction mixture is stirred for 20 minutes at RT. Then N-(2-chloroethyl)-morpholine-hydrochloride (1.07 g, 5.75 mmol) is added in four batches over a period of 20 minutes. After 70 hours stirring at RT and 1.5 hours at 45° C. the reaction mixture is diluted with 150 ml of ethyl acetate and extracted three times with ice water. The organic phase is dried on magnesium sulphate and the solvent is eliminated in vacuo. The crude product is acidified with TFA while cooling with ice in acetonitrile and DMF and chromatographed on Microsorb C18-reverse-phase [acetonitrile (0.1% TFA)/water (0.13% TFA)=10:90→100:0].

Yield: 641 mg (32% of theory)

$C_{34}H_{42}N_4O_6S \times 2\ C_2HF_3O_2$ (862.83)

Mass spectrum: $(M+H)^+=635$ retention time (Method 1): 2.12 min

Example 57

(Dimethylcarbamoylmethyl) 1-{3-[(R)-2-[3-(phenyl-sulphonylamino)-phenyl]-2-hydroxy-ethylamino]-3-methyl-butyl}-1H-indole-5-carboxylate hydrotrifluoroacetate

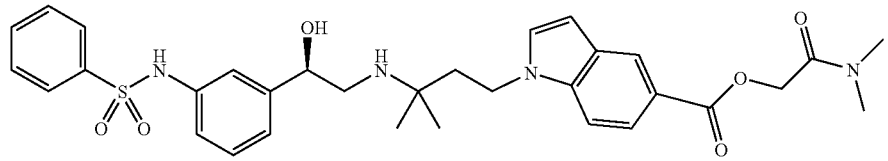

Potassium hydrogen carbonate (141 mg, 1.4 mmol) is added to a solution of 1-{3-[(R)-2-[3-(phenylsulphonylamino)-phenyl]-2-hydroxy-ethylamino]-3-methyl-butyl}-1H-indole-5-carboxylic acid-hydrotrifluoroacetate (Example 6; 300 mg, 0.47 mmol) in 2 ml DMF. Then the reaction mixture is stirred for 20 minutes at RT and 2-chloro-N,N-dimethylacetamide (143 mg, 1.18 mmol) is added. After 90 hours stirring at RT the reaction mixture is diluted with 50 ml of water and extracted with ethyl acetate. The organic phase is dried on magnesium sulphate and the solvent is eliminated in vacuo. The residue is chromatographed on silica gel (DCM/methanol=100:0→95:5).

Yield: 217 mg (76% of theory)
$C_{32}H_{38}N_4O_6S$ (606.73)
Mass spectrum: $(M+H)^+$=607
retention time (Method 1): 2.58 min

Example 58

(2-Diisopropylamino-ethyl) 1-{3-[(R)-2-[3-(phenyl-sulphonylamino)-phenyl]-2-hydroxy-ethylamino]-3-methyl-butyl}-1H-indole-5-carboxylate hydrotrifluoroacetate

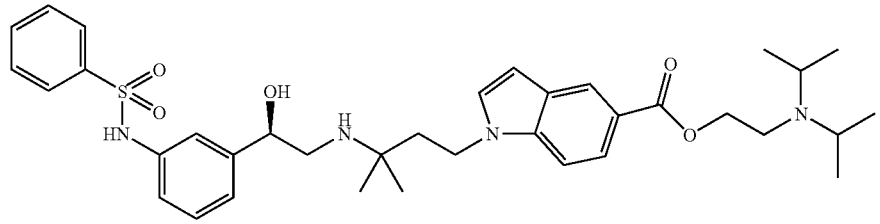

Potassium tert. butoxide (58 mg, 0.58 mmol) is added to a solution of 1-{3-[(R)-2-[3-(phenylsulphonylamino)-phenyl]-2-hydroxy-ethylamino]-3-methyl-butyl}-1H-indole-5-carboxylic acid [free base (Zwitterion) of Example 6; 300 mg, 0.58 mmol] in 2 ml DMF. Then the reaction mixture is stirred for 10 minutes at RT and 2-diisopropylamino-ethyl chloride hydrochloride (115 mg, 0.58 mmol) is added. After 72 hours stirring at RT the reaction mixture is diluted with 30 ml of ethyl acetate and extracted four times with 15 ml ice water. The organic phase is dried on magnesium sulphate, acidified with about 0.5 ml TFA and the solvent is eliminated in vacuo. The crude product is chromatographed on Microsorb C18-reverse-phase [acetonitrile (0.1% TFA)/water (0.13% TFA)= 10:90→100:0].

Yield: 45 mg (9% of theory)
$C_{36}H_{48}N_4O_5S \times 2\ C_2HF_3O_2$ (876.90)
Mass spectrum: $(M+H)^+$=649
retention time (Method 1): 2.29 min

TABLE 4

Prepared analogously to Examples 56-58 by alkylation of 1-{3-[(R)-2-[3-(phenylsulphonylamino)-phenyl]-2-hydroxy-ethylamino]-3-methyl-butyl}-1H-indole-5-carboxylic acid (Example 6) with the correspondingly substituted alkyl chloride (as the free base or hydrochloride salt; see $R_c$ group in Table 4).

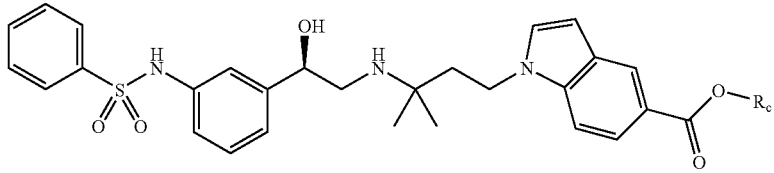

| Example | $R_c$ group | name | DC $R_f$ | MS $(M+H)^+$ | HPLC retention time (min.) | yield | formula free base | molar mass |
|---|---|---|---|---|---|---|---|---|
| 59 | | (2,2-dimethyl-propionyloxy-methyl 1-{3-[(R)-2-[3-(phenyl-sulphonylamino)-phenyl]-2-hydroxy-ethyl-amino]-3-methyl-butyl}-1H-indole-5-carboxylate) | | 636 | 3.28 meth. 1 | 29% | $C_{34}H_{41}N_3O_7S$ | 635.78 |
| 60 | | (butyryloxy-methyl) 1-{3-[(R)-2-[3-(phenyl-sulphonylamino)-phenyl]-2-hydroxy-ethyl-amino]-3-methyl-butyl}-1H-indole-5-carboxylate | | 622 | 3.18 meth. 1 | 58% | $C_{33}H_{39}N_3O_7S$ | 621.75 |
| 61 | | (1-ethoxy-carbonyloxy-ethyl) 1-{3-[(R)-2-[3-(phenyl-sulphonylamino)-phenyl]-2-hydroxy-ethyl-amino]-3-methyl-butyl}-1H-indole-5-carboxylate | | 638 | 3.14 meth. 1 | 61% | $C_{33}H_{39}N_3O_8S$ | 637.75 |
| 62 | | [2-(piperidin-1-yl)-ethyl ]1-{3-[(R)-2-[3-(phenyl-sulphonylamino)-phenyl]-2-hydroxy-ethyl-amino]-3-methyl-butyl}-1H-indole-5-carboxylate | 0.12 KG DCM/MeOH/NH$_3$ 95/5/0.1 | 633 | | 48% | $C_{35}H_{44}N_4O_5S$ | 632.82 |
| 63 | | [2-(pyrrolidin-1-yl)-ethyl ]1-{3-[(R)-2-[3-(phenylsulphonyl-amino)-phenyl]-2-hydroxy-ethyl-amino]-3-methyl-butyl}-1H-indole-5-carboxylate | 0.38 KG DCM/MeOH/NH$_3$ 90/10/0.1 | 619 | | 33% | $C_{34}H_{42}N_4O_5S$ | 618.79 |

TABLE 4-continued

Prepared analogously to Examples 56-58 by alkylation of 1-{3-[(R)-2-[3-(phenylsulphonylamino)-phenyl]-2-hydroxy-ethylamino]-3-methyl-butyl}-1H-indole-5-carboxylic acid (Example 6) with the correspondingly substituted alkyl chloride (as the free base or hydrochloride salt; see $R_c$ group in Table 4).

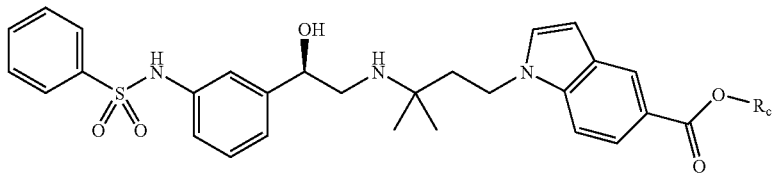

| Example | $R_c$ group | name | DC $R_f$ | MS $(M + H)^+$ | HPLC retention time (min.) | yield | formula free base | molar mass |
|---|---|---|---|---|---|---|---|---|
| 64 | | (2-diethylamino-ethyl)1-{3-[(R)-2-[3-(phenyl-sulphonylamino)-phenyl]-2-hydroxy-ethyl-amino]-3-methyl-butyl}-1H-indole-5-carboxylate | 0.54 KG DCM/NH$_3$ 90/10/0.1 | 621 | | 45% | $C_{34}H_{44}N_4O_5S$ | 620.81 |
| 65 | | [3-(morpholin-4-yl)-propyl] 1-{3-[(R)-2-[3-(phenyl sulphonylamino)-phenyl]-2-hydroxy-ethyl-amino]-3-methyl-butyl}-1H-indole-5-carboxylate | 0.57 KG DCM/MeOH/NH$_3$ 90/10/0.1 | 549 | | 60% | $C_{35}H_{44}N_4O_6S$ | 648.82 |
| 66 | | (2-dimethylamino-ethyl)1-{3-[(R)-2-[3-(phenyl-sulphonylamino)-phenyl]-2-hydroxy-ethyl-amino]-3-methyl-butyl}-1H-indole-5-carboxylate | 0.57 KG DCM/MeOH/NH$_3$ 90/10/0.1 | 649 | | 60% | $C_{32}H_{40}N_4O_5S$ | 592.76 |
| 67 | | [3-(piperidin-1-yl)-propyl]]1-{3-[(R)-2-[3-(phenyl-sulphonylamino)-phenyl]-2-hydroxy-ethyl-amino]-3-methyl-butyl}-1H-indole-5-carboxylate | 0.18 KG DCM/MeOH/NH$_3$ 90/9/1 | 647 | | 34% | $C_{36}H_{46}N_4O_5S$ | 646.85 |
| 68 | | [2-(azepan-1-yl)-ethyl]1-{3-[(R)-2-[3-(phenyl-sulphonylamino)-phenyl]-2-hydroxy-ethyl-amino]-3-methyl-butyl}-1H-indole-5-carboxylate | 0.27 KG DCM/MeOH/NH$_3$ 90/10/0.1 | 607 | | 18% | $C_{36}H_{46}N_4O_5S$ | 646.85 |
| 69 | | (3-dimethylamino-propyl)1-{3-[(R)-2-[3-(phenyl-sulphonylamino)-phenyl]-2-hydroxy-ethyl-amino]-3-methyl-butyl}-1H-indole-5-carboxylate | 0.28 KG DCM/MeOH/NH$_3$ 90/10/0.1 | 607 | | 19% | $C_{33}H_{42}N_4O_5S$ | 606.78 |

TABLE 4-continued

Prepared analogously to Examples 56-58 by alkylation of 1-{3-[(R)-2-[3-(phenylsulphonylamino)-phenyl]-2-hydroxy-ethylamino]-3-methyl-butyl}-1H-indole-5-carboxylic acid (Example 6) with the correspondingly substituted alkyl chloride (as the free base or hydrochloride salt; see $R_c$ group in Table 4).

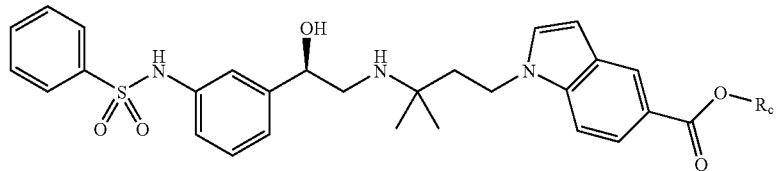

| Example | $R_c$ group | name | DC $R_f$ | MS (M + H)$^+$ | HPLC retention time (min.) | yield | formula free base | molar mass |
|---|---|---|---|---|---|---|---|---|
| 70 | | (2-diisobutylamino-ethyl)1-{3-[(R)-2-[3-phenyl-sulphonylamino)-phenyl]-2-hydroxy-ethyl-amino]-3-methyl-butyl}-1H-indole-5-carboxylate | 0.46 KG DCM/MeOH/Nh$_3$ 90/10/0.1 | 677 | | 46% | $C_{38}H_{52}N_4O_5S$ | 676.92 |
| 71 | | (2-dibutylamino-ethyl)1-{3-[(R)-2-[3-(phenyl-sulphonylamino)-phenyl]-2-hydroxy-ethyl-amino]-3-methyl-butyl}-1H-indole-5-carboxylate | 0.51 KG DCM/MeOH/NH$_3$ 90/9/1 | 677 | | 31% | $C_{38}N_{52}N_4O_5S$ | 676.92 |
| 72 | | [2-(2-oxo-pyrrolidin-1-yl)-ethyl]1-{3-[(R)-2-[3-(phenyl-sulphonylamino)-phenyl]-2-hydroxy-ethyl-amino]-3-methyl-butyl}-1H-indole-5-carboxylate | | 633 | 2.64 meth. 1 | 28% | $C_{34}H_{40}N_4O_6S$ | 632.78 |
| 73 | | [2-(4-methyl-piperazin-1-yl)-ethyl]1-{3-[(R)-2-[3-(phenyl-sulphonylamino)-phenyl]-2-hydroxy-ethyl-amino]-3-methyl-butyl}-1H-indole-5-carboxylate | | 648 | 2.10 meth. 1 | 24% | $C_{35}H_{45}N_5O_5S$ | 647.84 |
| 74 | | (pyridin-4-yl-methyl)1-{3-[(R)-2-[3-(phenyl-sulphonylamino)-phenyl]-2-hydroxy-ethyl-amino]-3-methyl-butyl}-1H-indole-5-carboxylate | | 613 | 2.33 meth. 1 | 22% | $C_{34}H_{36}N_4O_5S$ | 612.75 |

TABLE 4-continued

Prepared analogously to Examples 56-58 by alkylation of 1-{3-[(R)-2-[3-(phenylsulphonylamino)-phenyl]-2-hydroxy-ethylamino]-3-methyl-butyl}-1H-indole-5-carboxylic acid (Example 6) with the correspondingly substituted alkyl chloride (as the free base or hydrochloride salt; see $R_c$ group in Table 4).

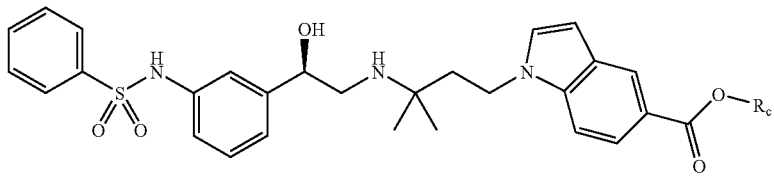

| Example | $R_c$ group | name | DC $R_f$ | MS (M + H)⁺ | HPLC retention time (min.) | yield | formula free base | molar mass |
|---|---|---|---|---|---|---|---|---|
| 75 | [2-(N-benzyl-N-methylamino)-ethyl] | [2-(N-benzyl-N-methylamino)-ethyl]1-{3-[(R)-2-[3-(phenyl-sulphonylamino)-phenyl]-2-hydroxy-ethyl-amino]-3-methyl-butyl}-1H-indole-5-carboxylate | | 669 | 2.36 meth. 1 | 35% | $C_{48}H_{44}N_5O_5S$ | 668.85 |
| 76 | [2-(2-methoxy-ethoxy)-ethyl] | [2-(2-methoxy-ethoxy)-ethyl]1-{3-[(R)-2-[3-(phenylsulphonyl-amino)-phenyl]-2-hydroxy-ethyl-amino]-3-methyl-butyl}-1H-indole-5-carboxylate | | 624 | 2.82 meth. 1 | 29% | $C_{33}H_{41}N_3O_7S$ | 623.77 |

Example 77

N-(3-{(R)-1-hydroxy-2-[3-(5-methanesulphinyl-indol-1-yl)-1,1-dimethyl-propyl-amino]-ethyl}-phenyl)-benzenesulphonamide-hydrotrifluoroacetate

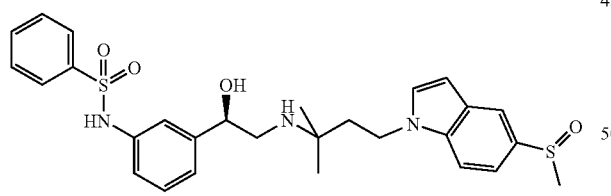

Oxone® (48 mg) is added to a solution of N-(3-{(R)-2-[3-(5-(methylsulphanyl)-indol-1-yl)-1,1-dimethyl-propylamino]-1-hydroxy-ethyl}-phenyl)-benzenesulphonamide-hydrotrifluoroacetate (Example 9) (50 mg, 0.08 mmol) in 10 ml acetone. The reaction mixture is stirred for 6 hours at RT and then combined with sodium sulphite (100 mg). Then the solvent is eliminated in vacuo, the residue is dissolved in water (1 ml) and DMF (1.5 ml), acidified with TFA and chromatographed on Microsorb C18-reverse-phase [acetonitrile (0.1% TFA)/water (0.13% TFA)=10:90→100:0].

Yield: 20 mg (39% of theory)

$C_{28}H_{33}N_3O_4S_2 \times CF_3CO_2H$ (653.74)

Mass spectrum: (M+H)⁺=540

$R_f$=0.37 (silica gel; DCM/methanol/ammonia=90:9:1)

Example 78

N-(3-{(R)-1-hydroxy-2-[3-(5-methanesulphonyl-indol-1-yl)-1,1-dimethyl-propyl-amino]-ethyl}-phenyl)-benzenesulphonamide-hydrotrifluoroacetate

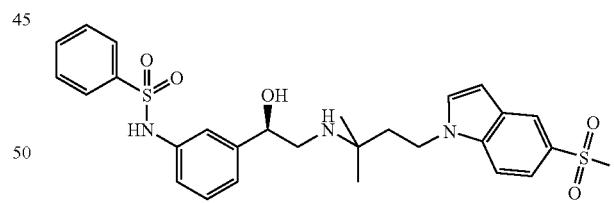

Oxone® (200 mg) is added to a solution of N-(3-{(R)-2-[3-(5-(methylsulphanyl)-indol-1-yl)-1,1-dimethyl-propylamino]-1-hydroxy-ethyl}-phenyl)-benzenesulphonamide-hydrotrifluoroacetate (Example 9) (50 mg, 0.08 mmol) in 10 ml acetone. The reaction mixture is stirred for 24 hours at 40° C. and then combined with sodium sulphite (100 mg). Then the solvent is eliminated in vacuo, the residue is dissolved in water (1 ml) and DMF (1.5 ml), acidified with TFA and chromatographed on Microsorb C18-reverse-phase [acetonitrile (0.1% TFA)/water (0.13% TFA)=10:90→100:0].

Yield: 12 mg (23% of theory)

$C_{28}H_{33}N_3O_5S_2 \times CF_3CO_2H$ (669.73)

Mass spectrum: (M+H)⁺=556

$R_f$=0.43 (silica gel; DCM/methanol/ammonia=90:9:1)

TABLE 5

Prepared by saponification of the corresponding esters with an excess of aqueous sodium hydroxide solution in methanol. After acidifying with TFA the compounds are chromatographed on Microsorb C18-reverse-phase [acetonitrile (0.1% TFA)/water (0.13% TFA) = 10:90 → 100:0]. All the active substances are isolated as hydrotrifluoroacetates.

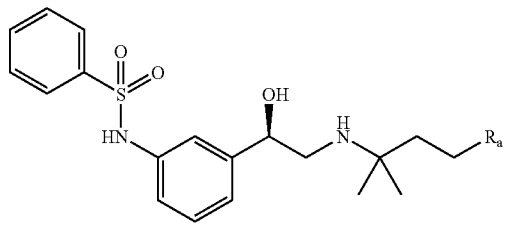

| Ex. | educt | $R_a$ group | name | Dc $R_f$ | MS $(M+H)^+$ | HPLC retention time (min.) | yield | formula free base | molar mass |
|---|---|---|---|---|---|---|---|---|---|
| 79 | 12 | | 1-{3-[(R)-2-[3-(phenylsulphonyl-amino)-phenyl]-2-hydroxy-ethyl-amino]-3-methyl-butyl}-1H-indole-6-carboxylic acid | 0.15 KG DCM/MeOH/NH$_3$ 9/1/0.1 | 522 | | 34% | $C_{28}H_{31}N_3O_5S$ | 521.63 |
| 80 | 14 | | 1-{3-[(R)-2-[3-(phenylsulphonyl-amino)-phenyl]-2-hydroxy-ethyl-amino]-3-methyl-butyl}-1H-indole-3-carboxylic acid | 0.23 KG DCM/MeOH/NH$_3$ 9/1/0.1 | 522 | | 59% | $C_{28}H_{31}N_3O_5S$ | 521.63 |
| 81 | 39 | | (S)-2-[(1-{3-[(R)-2-[3-(phenylsulphonyl-amino)-phenyl]-2-hydroxy-ethyl-amino]-3-methyl-butyl}-1H-indol-5-ylcarbonyl)-amino]-propionic acid | | 593 | 2.44 meth. 1 | 86% | $C_{31}H_{36}N_4O_6S$ | 592.71 |
| 82 | 40 | | (S)-2-[(1-{3-[(R)-2-[3-(phenylsulphonyl-amino)-phenyl]-2-hydroxy-ethyl-amino]-3-methyl-butyl}-1H-indol-5-ylcarbonyl)-amino]-3-methyl-butyric acid | | 621 | 2.67 meth. 1 | 75% | $C_{33}H_{40}N_4O_6S$ | 620.77 |
| 83 | 41 | | (2S,3S)-2-[(1-{3-[(R)-2-[3-(phenyl-sulphonylamino)-phenyl]-2-hydroxy-ethylamino]-3-methyl-butyl}-1H-indol-5-yl-carbonyl)-amino]-3-methyl-valeric acid | | 635 | 2.81 meth. 1 | 30% | $C_{34}H_{42}N_4O_6S$ | 634.79 |

TABLE 5-continued

Prepared by saponification of the corresponding esters with an excess of aqueous sodium hydroxide solution in methanol. After acidifying with TFA the compounds are chromatographed on Microsorb C18-reverse-phase [acetonitrile (0.1% TFA)/water (0.13% TFA) = 10:90 → 100:0]. All the active substances are isolated as hydrotrifluoroacetates.

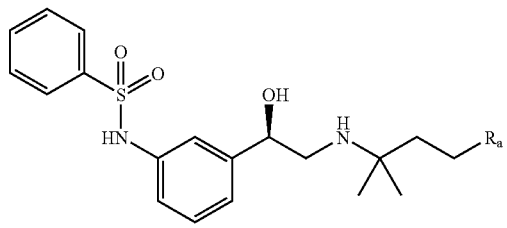

| Ex. | educt | $R_a$ group | name | Dc $R_f$ | MS $(M + H)^+$ | HPLC retention time (min.) | yield | formula free base | molar mass |
|---|---|---|---|---|---|---|---|---|---|
| 84 | 16 | | (1-{3-[(R)-2-[3-(phenylsulphonyl-amino)-phenyl]-2-hydroxy-ethyl-amino]-3-methyl-butyl}-1H-indol-3-yl)-acetic acid | 0.47 KG DCM/MeOH/NH₃ 90/10/0.1 | 536 | | 25% | $C_{29}H_{33}N_3O_5S$ | 535.66 |
| 85 | 44 | | 3-[(1-{3-[(R)-2-[3-(phenylsulphonyl-amino)-phenyl]-2-hydroxy-ethyl-amino]-3-methyl-butyl}-1H-indol-5-ylcarbonyl)-aminol-propionic acid | | 593 | 2.33 meth. 1 | 29% | $C_{31}H_{36}N_4O_6S$ | 592.71 |
| 86 | 45 | | [(1-{3-[(R)-2-[3-(phenylsulphonyl-amino)-phenyl]-2-hydroxy-ethyl-amino]-3-methyl-butyl}-1H-indol-5-ylcarbonyl)-amino]-acetic acid | | 579 | 3.83 meth. 1 | 14% | $C_{30}H_{34}N_4O_6S$ | 578.69 |

Example 87

N-[3-((R)-2-{1,1-dimethyl-3-[5-(2,2,2-trifluoro-1-hydroxy-ethyl)-indol-1-yl]-propylamino}-1-hydroxy-ethyl)-phenyl]-benzenesulphonamide-hydrotrifluoroacetate

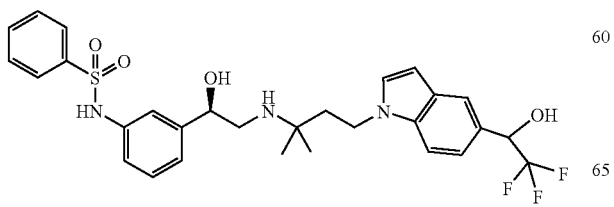

Sodium borohydride (6 mg, 0.16 mmol) is added to a solution of N-[3-((R)-2-{1,1-dimethyl-3-[5-(2,2,2-trifluoro-acetyl)-indol-1-yl]-propylamino}-1-hydroxy-ethyl)-phenyl]-benzenesulphonamide-hydrotrifluoroacetate (Example 17) (50 mg, 0.073 mmol) in 3 ml of methanol. After one hour's stirring at RT the reaction mixture is acidified with TFA and chromatographed on Microsorb C18-reverse-phase [acetonitrile (0.1% TFA)/water (0.13% TFA)=10:90→100:0].

Yield: 42 mg (84% of theory)

$C_{29}H_{32}F_3N_3O_4S \times CF_3CO_2H$ (689.67)

Mass spectrum: $(M+H)^+=576$ $R_f=0.08$ (silica gel; DCM/methanol/ammonia=95:5:0.1)

Example 88

N-(3-{(R)-1-hydroxy-2-[3-(5-hydroxymethyl-indol-1-yl)-1,1-dimethyl-propyl-amino]-ethyl}-phenyl)-benzenesulphonamide-hydrotrifluoroacetate

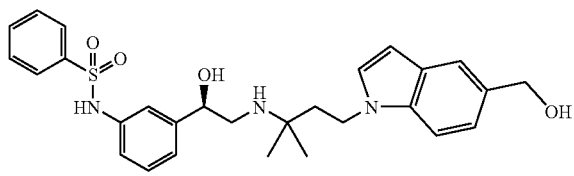

Sodium borohydride (60 mg, 0.42 mmol) is added batchwise over a period of 10 minutes to a solution of N-phenyl-sulphonyl-N-(3-{(R)-2-[3-(5-formyl-indol-1-yl)-1,1-dimethyl-propylamino]-1-hydroxy-ethyl}-phenyl)-benzenesulphonamide (Component VII) (270 mg, 0.42 mmol) in 2 ml of methanol. After one hour's stirring at RT the reaction mixture is diluted with 2 ml of methanol. After the addition of 2 ml of 4N sodium hydroxide solution and 0.5 ml DMF the reaction mixture is stirred for 2 hours at RT. The solvent is eliminated in vacuo, the residue is acidified with TFA and chromatographed on Microsorb C18-reverse-phase [acetonitrile (0.1% TFA)/water (0.13% TFA)=10:90→100:0].

Yield: 190 mg (73% of theory)
$C_{28}H_{33}N_3O_4S \times CF_3CO_2H$ (621.67)
Mass spectrum: $(M+H)^+ = 508$
retention time (Method 1): 2.50 min

Example 89

1-{3-[(R)-2-[3-(phenylsulphonylamino)-phenyl]-2-hydroxy-ethylamino]-3-methyl-butyl}-N-hydroxy-1H-indole-5-carboxamidine

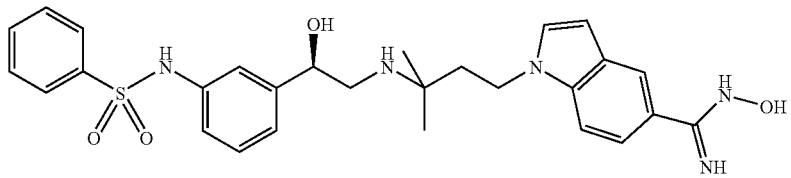

Hydroxylamine (600 μl) is added to a solution of N-(3-{(R)-2-[3-(5-cyano-indol-1-yl)-1,1-dimethyl-propylamino]-1-hydroxy-ethyl}-phenyl)-benzenesulphonamide (Example 1) (170 mg, 0.34 mmol) in 5 ml of ethanol. The reaction mixture is refluxed for 5 hours. Then the solvent is eliminated in vacuo.

Yield: 180 mg (99% of theory)
$C_{28}H_{33}N_5O_4S$ (535.66)
Mass spectrum: $(M+H)^+ = 536$
$R_f = 0.30$ (silica gel; DCM/methanol/ammonia=90:10:0.1)

Example 90

N-[3-((R)-2-{1,1-dimethyl-3-[5-(5-oxo-4,5-dihydro-[1,3,4]oxadiazol-2-yl)-indol-1-yl]-propylamino}-1-hydroxy-ethyl)-phenyl]-benzenesulphonamide-hydrotrifluoroacetate

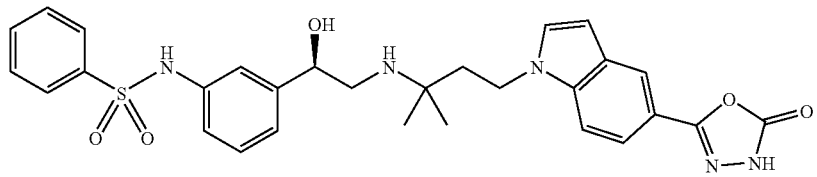

A solution of trichloromethyl chloroformate (diphosgene) (37 μl, 0.31 mmol) in 2 ml dioxane is added dropwise at RT over a period of 40 minutes to a solution of N-(3-{(R)-2-[3-(5-hydrazinocarbonyl-indol-1-yl)-1,1-dimethyl-propylamino]-1-hydroxy-ethyl}-phenyl)-benzenesulphonamide-hydrotrifluoroacetate (Example 38) (220 mg, 0.34 mmol) in 4 ml dioxane. After the addition of 2 ml DCM the reaction mixture is stirred for 23 hours at RT. The solvent is eliminated in vacuo and the residue is chromatographed on Microsorb C18-reverse-phase [acetonitrile (0.1% TFA)/water (0.13% TFA)=10:90→100:0].

Yield: 100 mg (48% of theory)
$C_{29}H_3,N_5O_5S \times CF_3CO_2H$ (675.68)
Mass spectrum: $(M+H)^+ = 562$
retention time (Method 1): 2.60 min

Example 91

1-{3-[(R)-2-[3-(phenylsulphonylamino)-phenyl]-2-hydroxy-ethylamino]-3-methyl-butyl}-1H-indole-5-carboxamidine-hydrotrifluoroacetate

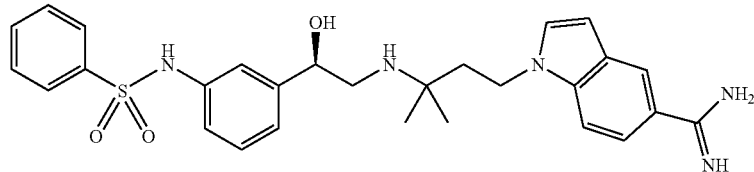

10% palladium on charcoal (40 mg) is added to a solution of 1-{3-[(R)-2-[3-(phenylsulphonylamino)-phenyl]-2-hydroxy-ethylamino]-3-methyl-butyl}-N-hydroxy-1H-indole-5-carboxamidine (Example 89) (120 mg, 0.22 mmol) in 5 ml of methanol. The reaction mixture is stirred for 24 hours at RT and 3 bar hydrogen. After the catalyst has been filtered off the solvent of the filtrate is eliminated in vacuo. The residue is chromatographed on Microsorb C18-reverse-phase [acetonitrile (0.1% TFA)/water (0.13% TFA)=10:90→100:0].

Yield: 90 mg (54% of theory)
$C_{28}H_{33}N_5O_3S \times 2\ CF_3CO_2H$ (747.71)
Mass spectrum: $(M+H)^+ = 520$
$R_f = 0.34$ (silica gel; DCM/methanol/ammonia=80:20:0.1)

Example 92

N-(1-{3-[(R)-2-[3-(phenylsulphonylamino)-phenyl]-2-hydroxy-ethylamino]-3-methyl-butyl}-1H-indol-5-yl)-oxalamidic acid hydrotrifluoroacetate

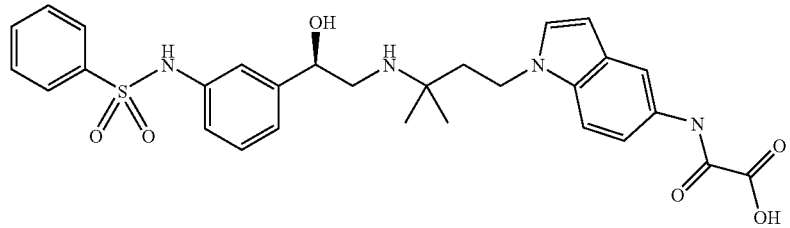

The free base of N-(3-{(R)-2-[3-(5-amino-indol-1-yl)-1,1-dimethyl-propylamino]-1-hydroxy-ethyl}-phenyl)-benzenesulphonamide-hydrotrifluoroacetate (free base from Example 20; 100 mg, 0.20 mmol) and pyridine (33 μl, 0.41 mmol) are dissolved in 3 ml THF. At 0° C. methyl oxalate chloride (21 μl, 0.22 mmol) is added and the reaction mixture is stirred for 3 hours at RT. The solvent is eliminated in vacuo and the residue is dissolved in 3 ml of methanol. Sodium hydroxide solution (4N; 1.5 ml) is added dropwise to the mixture. Then the reaction mixture is stirred for 18 hours at RT and then acidified with TFA. The solution is chromatographed on Microsorb C18-reverse-phase [acetonitrile (0.1% TFA)/water (0.13% TFA)=10:90→100:0].

Yield: 35 mg (25% of theory)
$C_{29}H_{32}N_4O_6S \times CF_3CO_2H$ (678.68)
Mass spectrum: $(M+H)^+ = 565$
$R_f = 0.41$ (silica gel; DCM/methanol/ammonia=80:20:0.1)

Example 93

N-(1-{3-[(R)-2-[3-(phenylsulphonylamino)-phenyl]-2-hydroxy-ethylamino]-3-methyl-butyl}-1H-indol-5-ylcarbonyl)-4-methyl-benzenesulphonamide-hydrotrifluoroacetate

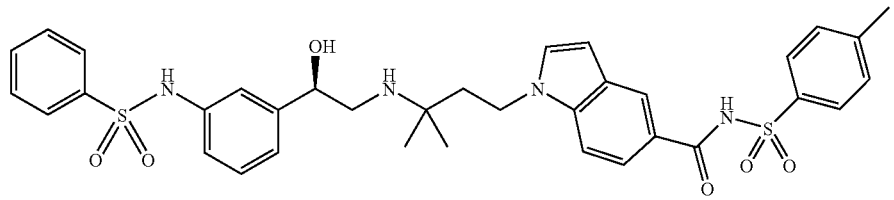

N,N'-carbonyldiimidazole (153 mg, 0.94 mmol) is added to a solution of 1-{3-[(R)-2-[3-(phenylsulphonylamino)-phenyl]-2-hydroxy-ethylamino]-3-methyl-butyl}-1H-indole-5-carboxylic acid-hydrotrifluoroacetate (Example 6) (300 mg, 0.47 mmol) in a mixture of 2 ml DCM and 2 ml THF. After 1.5 hours stirring at RT, 4-toluenic acid sulphonamide (161 mg, 0.94 mmol) is added. After another 2 hours stirring at RT, DBU (144 mg, 0.94 mmol) is added and the reaction mixture is again stirred for 18 hours at RT. The solvent is eliminated in vacuo, the residue is acidified with TFA and chromatographed on Microsorb C18-reverse-phase [acetonitrile (0.1% TFA)/water (0.13% TFA)=10:90→100:0].

Yield: 32 mg (9% of theory)
$C_{35}H_{38}N_4O_6S_2 \times CF_3CO_2H$ (788.86)
Mass spectrum: $(M+H)^+=675$
retention time (Method 1): 3.00 min Example 94

[2-(3-oxo-morpholin-4-yl)-ethyl]1-{3-[(R)-2-[3-(phenylsulphonylamino)-phenyl]-2-hydroxy-ethylamino]-3-methyl-butyl}-1H-indole-5-carboxylate hydro-trifluoroacetate

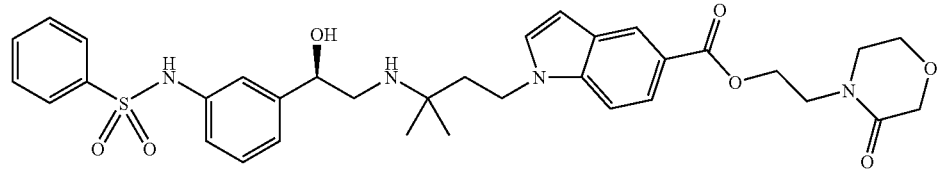

DMAP (14 mg, 0.11 mmol) and N-(2-hydroxyethyl)-morpholin-3-one (192 mg, 1.32 mmol) are added to a suspension of 1-{3-[(R)-2-[3-(phenylsulphonylamino)-phenyl]-2-hydroxy-ethylamino]-3-methyl-butyl}-1H-indole-5-carboxylic acid [free base (zwitterion) of Example 6; 600 mg, 1.15 mmol] in 6 ml DCM. While cooling with ice and stirring EDCI (243 mg, 1.27 mmol) is added batchwise over a period of 15 minutes. After 2 hours at 0° C. the reaction mixture is stirred for 18 hours at RT. The solvent is eliminated in vacuo, the residue is acidified with TFA and chromatographed on Microsorb C18-reverse-phase [acetonitrile (0.1% TFA)/water (0.13% TFA)=10:90 →100:0].

Yield: 86 mg (10% of theory)
$C_{34}H_{40}N_4O_7S \times CF_3CO_2H$ (762.79)
Mass spectrum: $(M+H)^+=649$
retention time (Method 1): 2.63 min Example 95

(E)-3-(1-{3-[(R)-2-[3-(phenylsulphonylamino)-phenyl]-2-hydroxy-ethylamino]-3-methyl-butyl}-1H-indol-5-yl)-acrylic acid hydrotrifluoroacetate

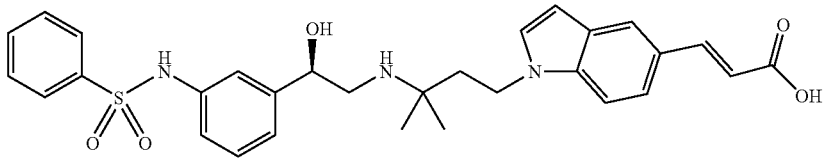

Triethylphosphonoacetate (716 mg, 3.2 mmol) is added dropwise over a period of 5 minutes to a suspension of sodium hydride (128 mg of a 60% suspension in mineral oil, 3.2 mmol) in 5 mL THF while cooling with ice. A solution of N-benzenesulphonyl-N-(3-{(R)-2-[3-(5-formyl-indol-1-yl)-1,1-dimethyl-propylamino]-1-hydroxy-ethyl}phenyl)-benzenesulphonamide (Component VII) (550 mg, 0.852 mmol) in 1 ml THF is added to this solution over a period of 5 minutes. After 69 hours stirring at RT 2 ml 4N sodium hydroxide solution (8 mmol) and 3 ml of ethanol are added. After another 18 hours stirring at RT the solvent is eliminated in vacuo, the residue is acidified with TFA and chromatographed on Microsorb C18-reverse-phase [acetonitrile (0.1% TFA)/water (0.13% TFA)=10:90→100:0].

Yield: 161 mg (29% of theory)
$C_{30}H_{33}N_3O_5S \times CF_3CO_2H$ (661.69)
Mass spectrum: $(M+H)^+=548$
retention time (Method 1): 2.67 min

Example 96

(1-{3-[(R)-2-[3-(phenylsulphonylamino)-phenyl]-2-hydroxy-ethylamino]-3-methyl-butyl}-1H-indol-5-yloxy)-acetic acid

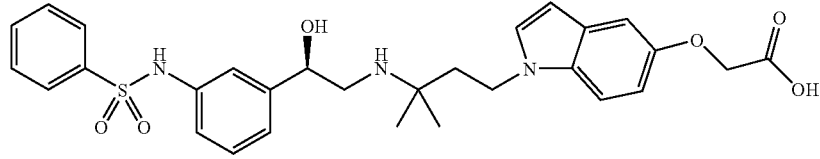

a. methyl (1H-indol-5-yloxy)-acetate

A suspension of 5-hydroxyindole (5.00 g; 37.6 mmol), caesium carbonate (26.9 g, 82.6 mmol) and ethyl bromoacetate (4.60 g, 30.0 mmol) in 100 ml acetone is stirred for 18 hours at ambient temperature. Then the reaction mixture is combined with water and DCM. The phases are separated and the aqueous phase is extracted with DCM. The combined phases are dried on sodium sulphate and freed from the solvent in vacuo.
Yield: 6.00 g (78% of theory)
$C_{11}H_{11}NO_3$ (205.21)
Mass spectrum: $(M+H)^+=206$ b. methyl [1-(3-amino-3-methyl-butyl)-1H-indol-5-yloxy]-acetate

Prepared analogously to Component V by alkylation of methyl (1H-indol-5-yloxy)-acetate with N-tert-butoxycarbonyl-4,4-dimethyl-[1,2,3]oxathiazinane-2,2-dioxide and subsequent cleaving of the acid protecting group.
Yield: 0.8% of theory
$C_{16}H_{22}N_2O_3$ (290.36)
Mass spectrum: $(M+H)^+=291$ c. (1-[3-[2-[3-(phenylsulphonylamino)-phenyl]-2-hydroxy-ethylamino]-3-methyl-butyl]-1H-indol-5-yloxy)-acetic acid Prepared analogously to Example 1 from methyl[1-(3-amino-3-methyl-butyl)-1H-indol-5-yloxy]-acetate by reaction with N—[(R)-3-oxiranyl-phenyl]-dibenzenesulphonamide and subsequent basic cleaving of the benzenesulphonyl group and of the methyl ester.
Yield: 20% of theory
$C_{29}H_{33}N_3O_6S$ (551.66)
Mass spectrum: $(M+H)^+=552$
retention time (Method 1): 2.55 min.

What is claimed is:
1. A compound of the formula

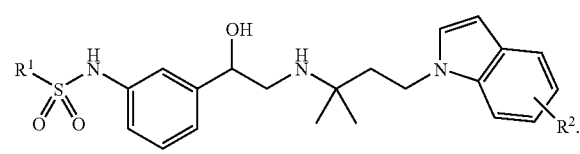

(I)

wherein
$R^1$ denotes a phenyl group, which may be mono- or disubstituted by fluorine, chlorine or bromine atoms or methyl, methoxy, trifluoromethoxy or difluoromethoxy groups, wherein the substituents may be identical or different, or
a heteroaryl group selected from pyridinyl and thienyl, and
$R^2$ denotes a hydrogen, fluorine, chlorine, bromine or iodine atom,
a nitro, cyano, trifluoromethoxy, difluoromethoxy, carboxy, 2,2,2-trifluoro-acetyl group, $C_{1-3}$-alkylsulphanyl, $C_{1-3}$-alkylsulphinyl, $C_{1-3}$-alkylsulphonyl, tetrazolyl, 5-oxo-4,5-dihydro-[1,3,4]oxadiazol-2-yl or 5-oxo-2,5-dihydro-[1,2,4]oxadiazol-3-yl group,
an amino group, which may be substituted by a carboxycarbonyl, aminocarbonyl, $C_{1-6}$-alkyl-aminocarbonyl, phenylaminocarbonyl, $C_{1-6}$-alkyl-carbonyl, benzyloxy-$C_{1-3}$-alkyl-carbonyl, cyano-$C_{1-3}$-alkyl-carbonyl, $C_{3-7}$-cycloalkyl-carbonyl or $C_{1-3}$-alkylsulphonyl group,
wherein the above-mentioned $C_{1-6}$-alkyl-carbonyl group may be straight-chain or branched and may be substituted by an amino group in the alkyl moiety,
a $C_{1-3}$-alkyl group, which may be substituted independently of one another by one or two trifluoromethyl, hydroxy, carboxy or $C_{1-6}$-alkyloxy-carbonyl groups,
a $C_{2-3}$-alkenyl group, which may be substituted by a carboxy group,
a $C_{1-3}$-alkyloxy group, which may be substituted by a carboxy or $C_{1-3}$-alkyloxy-carbonyl group,
a $C_{1-3}$-alkyl-carbonyl group, which is substituted by a $C_{1-3}$-alkylsulphonyl group,
$C_{1-6}$-alkyloxy-carbonyl group, which may be substituted in the alkyl moiety by a di-($C_{1-3}$-alkyl)-amino-carbonyl, $C_{1-6}$-alkyl-carbonyloxy, $C_{1-6}$-alkyloxy-carbonyloxy or pyridinyl group or by a 2-oxo-[1,3]dioxolyl group optionally substituted by a $C_{1-3}$-alkyl group,
$C_{2-6}$-alkyloxy-carbonyl group, which is substituted in the alkyl moiety from position 2 by a di-($C_{1-4}$-alkyl)-amino, N—($C_{1-3}$-alkyl)-N-benzyl-amino or $C_{1-3}$-alkyloxy-$C_{1-3}$-alkyloxy-group or by a 3- to 7-membered cycloalkyleneimino group,
wherein in the above-mentioned 5- to 7-membered cycloalkyleneimino group one or two methylene groups may be replaced independently of one another by an oxygen or sulphur atom and/or a carbonyl, sulphonyl or an —N($C_{1-3}$-alkyl) group,
an aminocarbonyl group, which may be substituted at the nitrogen atom independently of one another by one or two groups selected from cyano, hydroxy, $C_{1-6}$-alkyl, $C_{3-7}$-cycloalkyl, $C_{1-3}$-alkoxy, amino, di-($C_{1-3}$-alkyl)-amino, (4-methyl-phenyl)-sulphonyl,
wherein the above-mentioned alkyl group may be straight-chain or branched and may be substituted by one to three fluorine atoms or by a carboxy, $C_{1-3}$-alkoxy-carbonyl, $C_{3-7}$-cycloalkyl or $C_{1-3}$-alkylsulphonyl group, a carbonyl group which is substituted by a 3- to 7-membered cycloalkyleneimino group,
wherein in the above-mentioned 5- to 7-membered cycloalkyleneimino group a methylene group may be replaced by an oxygen or sulphur atom or a carbonyl or sulphonyl group,
or a group of formula

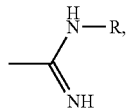

wherein R denotes a hydrogen atom or a hydroxy group,
wherein the alkyl groups contained in the above mentioned groups may each be straight-chain or branched,
or a salt thereof.

2. A compound of the formula (I) according to claim 1, wherein
$R^2$ is defined as in claim 1 and
$R^1$ denotes a phenyl group, which may be substituted by a fluorine, chlorine or bromine atom or a methyl, methoxy, trifluoromethoxy or difluoromethoxy group,
or a salt thereof.

3. A compound of the formula (I) according to claim 2, wherein
$R^1$ denotes a phenyl group,
or a salt thereof.

4. A compound of the formula (I) according to claim 1, wherein the group $R^2$ is in position 5 or 6 of the indole, or a salt thereof.

5. A compound of the formula (I) according to claim 4, wherein the group $R^2$ is in position 5 of the indole, or a salt thereof.

6. A compound of the formula (I) according to claim 1, wherein:
$R^2$ denotes a hydrogen atom or
a cyano, carboxy, $C_{1-4}$-alkyloxy-carbonyl, tetrazolyl, 5-oxo-2,5-dihydro-[1,2,4]oxadiazol-3-yl or 5-oxo-4,5-dihydro-[1,3,4]oxadiazol-2-yl group,
wherein the above mentioned $C_{2-4}$-alkyloxy-carbonyl groups in the alkyl moiety may be substituted from position 2 by a di-($C_{1-4}$-alkyl)-amino group and
an amino group, which may be substituted by a carboxycarbonyl, aminocarbonyl, $C_{1-3}$-alkylcarbonyl or cyanoacetyl group,
an aminocarbonyl group, which may be substituted at the nitrogen atom independently of one another by one or two groups selected from hydroxy, methyl, amino or cyclopropylmethyl,
or a carbonyl group, which is substituted by a morpholin-4-yl, pyrrolidin-1-yl or 1,1-dioxo-1-thiomorpholin-4-yl-group,
and wherein the alkyl group contained in the above mentioned groups may in each case be straight-chain or branched,
or a salt thereof.

7. A compound according to one of claims 1 to 6, wherein the compound in question is the (R)-enantiomer of formula

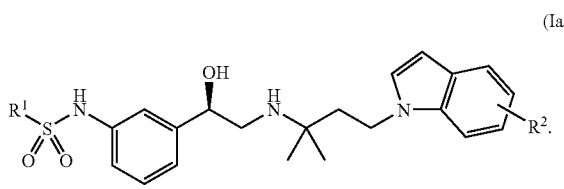

(Ia)

8. A compound according to one of claims 1 to 6, wherein the compound in question is the (S)-enantiomer of formula

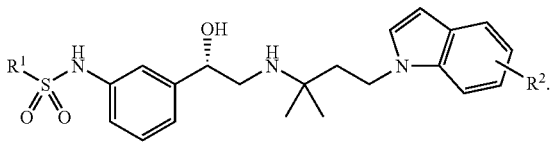

(Ib)

9. A compound selected from the group consisting of:
N-(1-{3-[(R)-2-[3-(phenylsulphonylamino)-phenyl]-2-hydroxy-ethylamino]-3-methyl-butyl}-1H-indol-5-yl)-2-cyano-acetamide;
1-{3-[(R)-2-[3-(phenylsulphonylamino)-phenyl]-2-hydroxy-ethylamino]-3-methyl-butyl}-1H-indole-5-carboxylic acid-cyclopropylmethyl-amide;
N-[3-((R)-2-{1,1-dimethyl-3-[5-(morpholin-4-ylcarbonyl)-indol-1-yl]-propylamino}-1-hydroxy-ethyl)-phenyl]-benzenesulphonamide;
1-{3-[(R)-2-[3-(phenylsulphonylamino)-phenyl]-2-hydroxy-ethylamino]-3-methyl-butyl}-1H-indole-5-carboxylic acid;
N-(3-{(R)-2-[1,1-dimethyl-3-(5-ureido-indol-1-yl)-propylamino]-1-hydroxy-ethyl}-phenyl)-benzenesulphonamide);
[2-(morpholin-4-yl)-ethyl]1-{3-[(R)-2-[3-(phenylsulphonylamino)-phenyl]-2-hydroxy-ethylamino]-3-methyl-butyl}-1H-indole-5-carboxylate;
N-(3-{(R)-2-[3-(5-amino-indol-1-yl)-1,1-dimethyl-propylamino]-1-hydroxy-ethyl}-phenyl)-benzenesulphonamide;
N-(3-{(R)-2-[3-(5-hydrazinocarbonyl-indol-1-yl)-1,1-dimethyl-propylamino]-1-hydroxy-ethyl}-phenyl)-benzenesulphonamide;
(2-dimethylamino-ethyl) 1-{3-[(R)-2-[3-(phenylsulphonylamino)-phenyl]-2-hydroxy-ethylamino]-3-methyl-butyl}-1H-indole-5-carboxylate; and
N-(1-{3-[(R)-2-[3-(phenylsulphonylamino)-phenyl]-2-hydroxy-ethylamino]-3-methyl-butyl}-1H-indol-5-yl)-oxalamidic acid;
or a salt thereof.

10. A physiologically acceptable salt of a compound according to one of claims 1 to 6 or 9.

11. A pharmaceutical composition comprising a compound according to one of claims 1 to 6 or 9 and a pharmaceutically acceptable carrier.

12. A method for treating type II diabetes, obesity, or overactive bladder, which method comprises administering to a host having such a disease a therapeutically effective amount of a compound according to one of claims 1 to 6 or 9.

13. A pharmaceutical composition comprising a compound according to claim 7 and a pharmaceutically acceptable carrier.

14. A pharmaceutical composition comprising a compound according to claim 8 and a pharmaceutically acceptable carrier.

15. A method for treating type II diabetes, obesity, or overactive bladder, which method comprises administering to a host having such a disease a therapeutically effective amount of a compound according to claim 7.

16. A method for treating type II diabetes, obesity, or overactive bladder, which method comprises administering to a host having such a disease a therapeutically effective amount of a compound according to claim 8.

* * * * *